(12) United States Patent
V et al.

(10) Patent No.: US 8,602,396 B1
(45) Date of Patent: Dec. 10, 2013

(54) CONTROLLING AIRBORNE MATTER

(75) Inventors: Philip Polito V, Tega Cay, SC (US);
Bradley Allen Kessler, Rock Hill, SC (US); Irving Edward Figge, Bluffton, SC (US)

(73) Assignee: ScentAir Technologies, Inc., Charlotte, NC (US)

( * ) Notice: Subject to any disclaimer, the term of this patent is extended or adjusted under 35 U.S.C. 154(b) by 538 days.

(21) Appl. No.: 12/783,280

(22) Filed: May 19, 2010

Related U.S. Application Data

(60) Provisional application No. 61/179,553, filed on May 19, 2009, provisional application No. 61/228,113, filed on Jul. 23, 2009, provisional application No. 61/252,562, filed on Oct. 16, 2009, provisional application No. 61/345,856, filed on May 18, 2010.

(51) Int. Cl.
*B01F 3/04* (2006.01)

(52) U.S. Cl.
USPC ............... 261/81; 261/DIG. 88; 239/DIG. 11

(58) Field of Classification Search
USPC ........ 261/30, 81, DIG. 88, DIG. 89; 222/504; 239/DIG. 11
See application file for complete search history.

(56) References Cited

U.S. PATENT DOCUMENTS

| | | | |
|---|---|---|---|
| 2,085,390 A | 6/1937 | Quinlivan | |
| 2,540,144 A | 2/1951 | Stern | |
| 2,562,959 A | 8/1951 | Stern | |
| 2,562,960 A | 8/1951 | Stern | |
| 2,813,452 A | 11/1957 | Laube | |
| 2,905,049 A | 9/1959 | Laube | |
| 3,138,009 A | 6/1964 | McCreight | |
| 3,628,829 A | 12/1971 | Heilig | |
| 3,666,144 A * | 5/1972 | Winder | 222/646 |
| 3,685,734 A | 8/1972 | Paciorek et al. | |
| 3,795,438 A | 3/1974 | Westenholz et al. | |
| 3,848,775 A * | 11/1974 | Possell | 222/649 |
| 3,974,941 A * | 8/1976 | Mettler | 222/646 |
| 4,059,422 A | 11/1977 | Steiner | |
| 4,065,261 A | 12/1977 | Fukada | |
| 4,110,419 A | 8/1978 | Miller | |
| 4,310,307 A | 1/1982 | Bellisario | |
| 4,356,969 A | 11/1982 | Obermayer et al. | |
| 4,413,784 A | 11/1983 | Dea | |
| 4,415,797 A * | 11/1983 | Choustoulakis | 392/394 |
| 4,603,030 A | 7/1986 | McCarthy | |
| 4,828,181 A | 5/1989 | Singels | |
| 4,874,129 A | 10/1989 | DiSapio et al. | |

(Continued)

FOREIGN PATENT DOCUMENTS

| | | |
|---|---|---|
| EP | 997198 A3 | 10/2000 |
| WO | WO2005105163 A1 | 11/2005 |

OTHER PUBLICATIONS

Petrucci, Ralph H. and Harwood, William S., General Chemistry, Seventh Edition, Prentice Hall, 1997, pp. 420-422.

(Continued)

*Primary Examiner* — Charles Bushey
(74) *Attorney, Agent, or Firm* — Fish & Richardson P.C.

(57) ABSTRACT

An apparatus for fragrancing an air space can include a magnetic field generator configured to generate a magnetic field, and a fragrance delivery system configured to release fragrant particles into an air space such that at least some of the fragrant particles enter the magnetic field generated by the magnetic field generator.

36 Claims, 20 Drawing Sheets

(56) References Cited

U.S. PATENT DOCUMENTS

| | | | |
|---|---|---|---|
| 4,952,024 A | 8/1990 | Gale | |
| 5,071,704 A | 12/1991 | Fischel | |
| 5,273,689 A | 12/1993 | Hamasaki | |
| 5,610,674 A | 3/1997 | Martin | |
| 5,713,971 A | 2/1998 | Rohrbach et al. | |
| 5,732,317 A | 3/1998 | Orchard et al. | |
| 5,749,519 A | 5/1998 | Miller | |
| 5,749,520 A | 5/1998 | Martin et al. | |
| 5,898,475 A | 4/1999 | Martin | |
| 6,090,331 A | 7/2000 | Schwarz et al. | |
| 6,361,752 B1 | 3/2002 | Demarest et al. | |
| 6,405,944 B1 | 6/2002 | Benalikhoudja | |
| 6,419,122 B1 * | 7/2002 | Chown | 222/162 |
| 6,444,156 B1 | 9/2002 | Schwarz et al. | |
| 6,632,405 B2 | 10/2003 | Lua | |
| 6,938,883 B2 * | 9/2005 | Adams et al. | 261/30 |
| 7,229,280 B2 | 6/2007 | Kubicek et al. | |
| 7,651,077 B1 | 1/2010 | Rosener et al. | |
| 7,938,340 B2 * | 5/2011 | Anderson et al. | 239/337 |
| 2002/0054273 A1 | 5/2002 | Martin | |
| 2002/0197189 A1 | 12/2002 | Lua | |
| 2005/0133752 A1 * | 6/2005 | Purvines et al. | 251/129.15 |
| 2006/0213841 A1 | 9/2006 | Gleich et al. | |
| 2006/0237090 A1 | 10/2006 | Benalikhoudja | |
| 2007/0243791 A1 | 10/2007 | Stedman | |

OTHER PUBLICATIONS

U.S. Final Office Action for U.S. Appl. No. 12/693,842 dated Aug. 20, 2010 (12 pages).

* cited by examiner

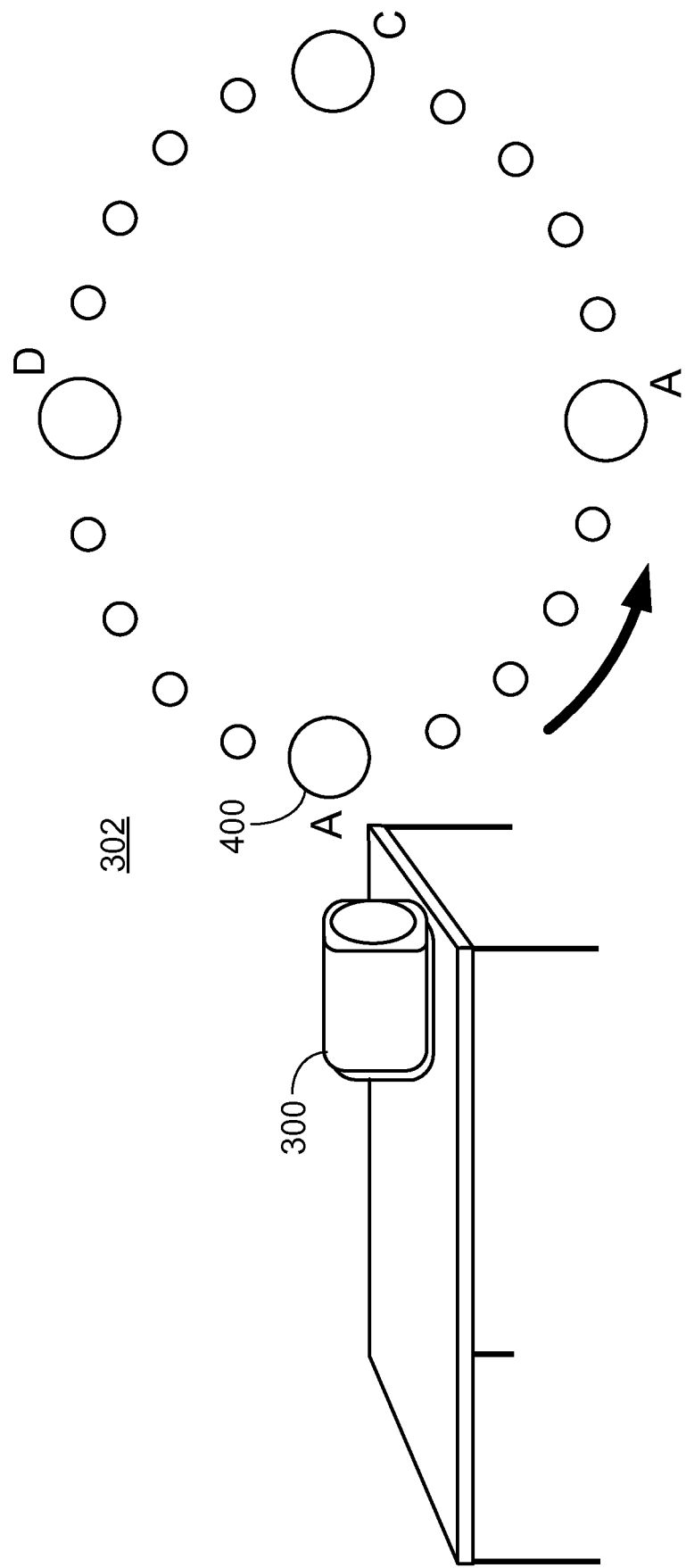

CONTROLLING AIRBORNE MATTER

CROSS REFERENCE TO RELATED APPLICATIONS

This is a utility application that claims the benefit of priority to U.S. provisional applications for U.S. Patent Application Ser. No. 61/179,553, filed on May 19, 2009, and titled "Controlling Fragrant Compounds," U.S. Patent Application Ser. No. 61/228,113, filed on Jul. 23, 2009, and titled "Controlling Fragrant Materials," U.S. Patent Application Ser. No. 61/252,562, filed Oct. 16, 2009, and titled "Controlling Fragrant Particles," and U.S. Patent Application Ser. No. 61/345,856, filed on May 18, 2010, and titled "Controlling Airborne Matter," which are hereby incorporated by reference.

TECHNICAL FIELD

This disclosure relates to controlling airborne matter, and, more particularly, to controlling fragrant matter in an airspace.

BACKGROUND

Scents and aromas can be delivered in the air in retail establishments, restrooms, restaurants, hotels, and airports to establish a particular environment or mood for customers and visitors. In retail establishments, for example, the scents and aromas can make the customer want to remain in a scented area for a longer period of time, thereby increasing the chances that the customer will view items for purchase. Scents and aromas can be delivered in an air space to complement various brands and seasonal items.

BRIEF DESCRIPTION OF THE DRAWINGS

FIG. 4 illustrates an example of how the magnetic field generated by the magnetic field generator incorporated within the fragrance delivery apparatus may influence a particle of fragrance oil after the particle of fragrance oil has been delivered into the airspace.

Like reference numbers and designations in the various drawings can indicate like elements.

SUMMARY

Figure 1:
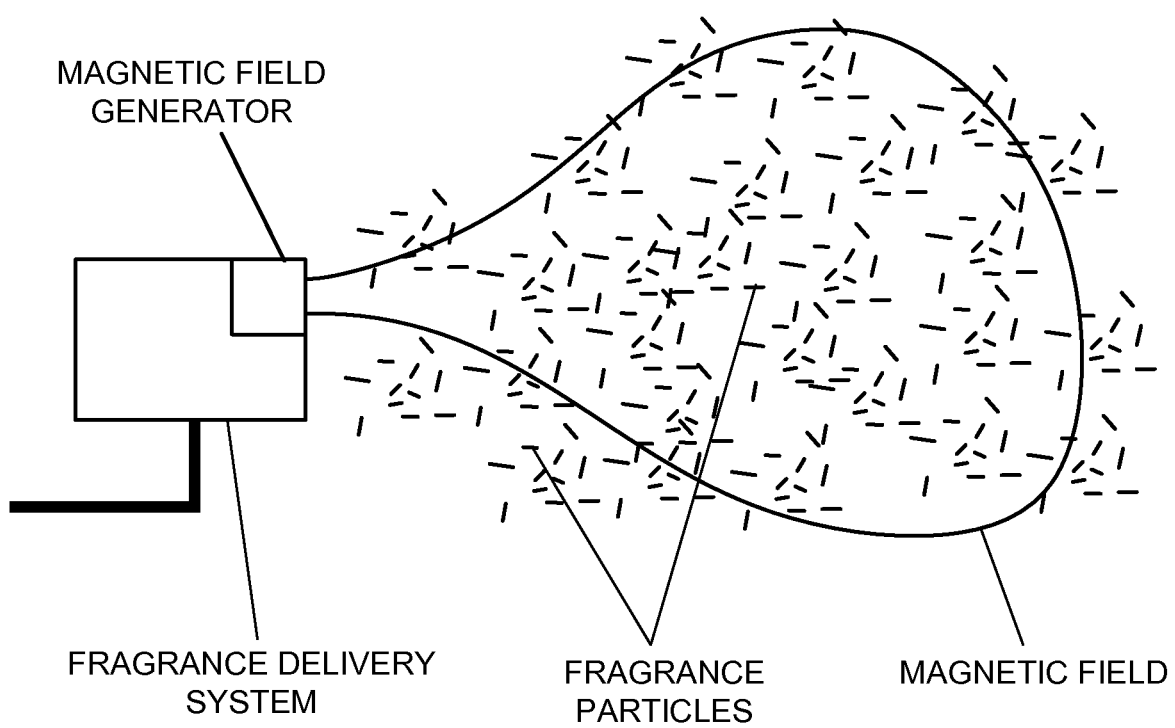
FIGS. 1 and 2 depict examples of a fragrance delivery system with a magnetic field generator.

In one general aspect, an apparatus for fragrancing an air space includes a magnetic field generator configured to generate a magnetic field and a fragrance delivery system configured to release fragrant particles into an air space such that at least some of the fragrant particles enter the magnetic field generated by the magnetic field generator.

Implementations may include one or more of the following features. For example, the magnetic field generator may include a conductive coil. In addition, the apparatus may include a voltage source having a positive terminal and a negative terminal and the positive terminal of the voltage source may be connected to a first terminal of the conductive coil and the negative terminal of the voltage source may be connected to a second terminal of the conductive coil such that an electric current flows through the conductive coil between the first terminal and the second terminal thereby generating the magnetic field.

In some implementations, the magnetic field generator may include a core, and the conductive coil may be wound around the core. The core may be formed from a conductive material or a non-conductive material. In addition, the core may include a first leg and a second leg that is mechanically coupled to the first leg. At least one winding of the conductive coil may be wound around the first leg of the core and at least one winding of the conductive coil may be wound around the second leg of the core. The first leg of the core and the second leg of the core may be formed from a contiguous piece of material, and the core may include a dividing post that bisects the contiguous piece of material thereby defining the first and second legs of the core. The conductive coil may be formed from a wire having a first end and a second end. From the perspective of the first end of the wire, the wire may be wound around the first leg of the core before the wire is wound around the second leg of the core, with windings around the first leg of the core beginning adjacent to the dividing post and extending generally outwardly along the first leg of the core away from the dividing post and the second leg of the core before returning inwardly along the first leg of the core towards the dividing post and the second leg of the core. Windings around the second leg of the core may begin adjacent to the dividing post and extend generally outwardly along the second leg of the core away from the dividing post and the first leg of the core before returning inwardly along the second leg of the core towards the dividing post and the first leg of the core. The first end of the wire may be electrically coupled to the negative terminal of the voltage source, and the second end of the wire may be electrically coupled to the positive terminal of the voltage source.

The contiguous piece of material from which the core is formed may be a loop of metal that defines an interior space inside of the loop of metal and an exterior space outside of the loop of metal. The dividing post may bisect the loop of metal such that a first section of the dividing post is located in the exterior space outside of the loop of metal, a second section of the dividing post is located in the interior space inside of the loop of metal, and a third section of the dividing post is located in the exterior space outside of the loop of metal at a position, relative to the loop of metal, that is substantially opposite from a position of the first section of the dividing post. In addition, at least one winding of the wire may be wrapped around the first section of the dividing post, and at least one winding of the wire may be wrapped around the third section of the dividing post. In such implementations, from the perspective of the first end of the wire, the wire may be wound around the first section of the dividing post before the wire is wound around the first leg of the core and the wire may be wound around the third section of the dividing post after the wire is wound around the second leg of the core.

In some implementations, the number of windings around the first leg of the core may be equal to the number of windings around the second leg of the core, while, in other implementations, the number of windings around the second leg of the core may not be equal to the number of windings around the second leg of the core.

The first leg of the core may be disposed at a fixed angle other than 180° relative to the second leg of the core. Alternatively, the mechanical coupling between the first leg of the core and the second leg of the core may enable an angle at which the first leg of the core is disposed relative to the second leg of the core to be changed, thereby enabling the properties of the magnetic field to be changed by changing the angle at which the first leg of the core is disposed relative to the second leg of the core. Furthermore, the length of the first leg of the core may be substantially the same as the length of the second leg of the core, or the length of the first leg of the core may be different than the length of the second leg of the core.

In some implementations, the apparatus may include a housing, and both the magnetic field generator and the fragrance delivery system may be at least partially incorporated within the housing. An opening may be defined within the housing exposing at least a portion of the magnetic field generator to an exterior of the housing. The housing may be configured to receive a voltage source. In addition, a voltage source may be received within the housing.

The apparatus may include a voltage source having a positive terminal and a negative terminal, and the fragrance delivery system may include a conductor for supplying an electrical bias to fragrant particles to be released by the fragrance delivery system. In addition, a first terminal of the conductor may be electrically coupled to the negative terminal of the voltage source and a second terminal of the conductor may provide an electrical bias to at least some of the fragrant particles to be released by the fragrance delivery system.

In some implementations, the apparatus may include an additional magnetic field generator that is configured to generate another magnetic field, that is physically distinct from the magnetic field generator, and that is located adjacent to the magnetic field generator. In such implementations, the magnetic field generator and the other magnetic field generator may be configured such that the magnetic field generated by the magnetic field generator and the other magnetic field generated by the other magnetic field generator are additive and combine to form a single magnetic field, and at least some of the released fragrant particles enter the single magnetic field.

In some implementations, the apparatus may include multiple additional magnetic field generators, each of which is configured to generate an additional magnetic field, is physically distinct from the magnetic field generator and other of the multiple additional magnetic field generators, and is displaced from other of the multiple additional magnetic field generators. In such implementations, the magnetic field generator and the multiple additional magnetic field generators may be configured to generate magnetic fields that are oriented such that at least some of the fragrant particles released into the magnetic field generated by the magnetic field generator are transferred to each of the additional magnetic fields. In addition, in some implementations, the magnetic field generator and the fragrance delivery system may not be physically connected.

According to still another general aspect, an apparatus for dispensing an inhalable medicine into an air space includes a magnetic field generator configured to generate a magnetic field, and an inhalable medicine delivery system configured to release inhalable medicine into an air space such that at least some of the inhalable medicine is released into the magnetic field generated by the magnetic field generator.

In another general aspect, a system for fragrancing an airspace includes a tubular-shaped wicking structure having an exterior surface and an interior surface that defines an air channel. The wicking structure is impregnated with a fragrance material and configured to enable quantities of the fragrance material to be released from the wicking structure into air flowing through the air channel. In addition, the system includes a housing at least partially enclosing the tubular-shaped wicking structure. The housing includes an end cap defining an air intake opening configured to enable air to enter the air channel and a nose cone defining an air output opening configured to enable air flowing through the air channel and the quantities of fragrance material that have been released into the air flowing the air channel to exit the air channel. The system also includes a magnetic field generator coupled to the nose cone, which may be located anywhere in or near the system.

The details of one or more implementations are set forth in the accompanying drawings and the description below. Other features will be apparent from the description and drawings, and from the claims.

DETAILED DESCRIPTION

The details of various example implementations are set forth in the accompanying drawings and the description below. In the following description, for the purposes of explanation, numerous specific details are set forth in order to provide a thorough understanding. It will be apparent, however, that the implementations may be generally practiced without these specific details. Other features, objects, and aspects are apparent from the description and drawings.

A magnetic field generator (e.g., a solenoid) can be used to generate a magnetic field in an airspace in order to control and manipulate fragrant particles (e.g., tiny droplets of fragrant oil) within the airspace.

As illustrated in FIG. 1, in one implementation, a fragrance delivery system delivers particles of fragrance oil into an airspace to fragrance the airspace, and a magnetic field generator (e.g., a solenoid) is used to generate a magnetic field in the airspace in order to control the fragrant particles within the airspace after their delivery. Individual molecules of the fragrance oil naturally may be negatively charged. In addition, an electric potential may be placed across a quantity of fragrance oil within the fragrance delivery system prior to delivering the fragrance oil into the airspace, thereby imparting additional negative charge on at least some of the individual oil molecules. During the delivery process, the mechanical stress of the delivery system may shear the fragrance oil. This mechanical stress, in addition to the negative charge of the individual fragrance oil molecules, may cause the fragrance oil molecules to readily donate their extra electrons to other substances willing to accept them.

When the fragrance oil molecules enter the magnetic field generated by the magnetic field generator, the magnetic field exerts an influence on the negatively charged fragrance oil molecules. This force may cause the particles to remain within the magnetic field, and thus suspended within the airspace, repeatedly being attracted and repelled by the magnetic field generated by the magnetic field generator.

Furthermore, the interaction of the fragrance oil molecules with the magnetic field generated by the magnetic field generator may allow for the manipulation and control of both the characteristics and physical properties of fragrance oil within the airspace. Through such manipulation and control of the fragrance oil, the longevity of the fragrance oil molecules in the airspace may be increased; the quantity of oil required to maintain a fragrance at a certain level within an airspace may be reduced; the reactivity of the fragrance oil molecules with other items in the environment may be reduced; the composition and intensity change of the fragrance over time may be controlled; the movement of the fragrance oil molecules through the airspace may be controlled; and the lifespan of the fragrance oil available to the fragrance delivery system may be increased. For example, the excitement of the fragrance oil molecules caused by the electric charge imparted on them and the mechanical stress of the delivery system may cause the fragrance oil molecules to be dispersed throughout a larger volume of the airspace than they otherwise might and to be perceived more strongly in a person's olfactory complex than they otherwise might.

Figure 2:
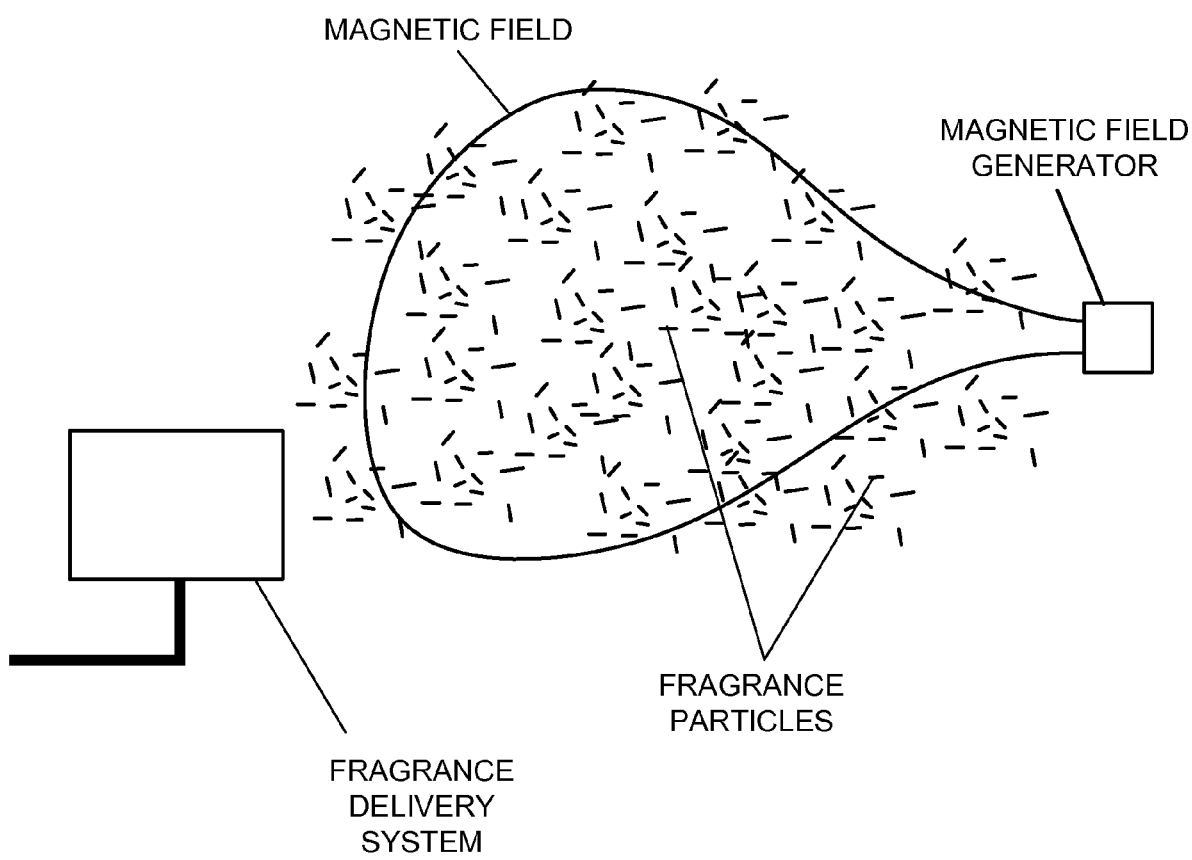

As illustrated in FIG. 1, in some implementations, the magnetic field generator may be incorporated within the same housing as the fragrance delivery system. In alternative implementations, for example as illustrated in FIG. 2, the magnetic field generator may be detached and physically distinct from the fragrance delivery system. In such implementations, the magnetic field generator may even be displaced by some distance from the fragrance delivery system and yet still be positioned in a location from which the magnetic field that it generates exerts an influence on the particles of fragrance oil delivered by the fragrance delivery apparatus.

Figure 3:
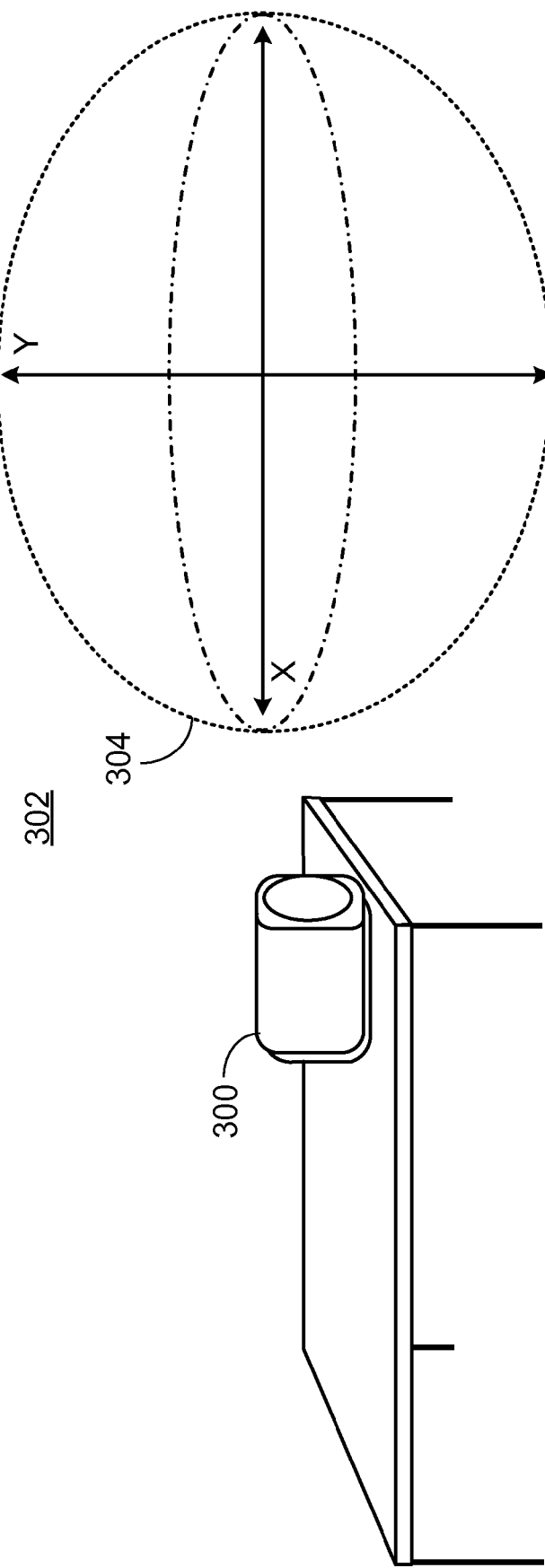
FIG. 3 depicts a block diagram of an example of a fragrance delivery system.

FIG. 3 is a block diagram of an example of a fragrance delivery system 300. As will be discussed in greater detail below, the fragrance delivery system 300 includes an air column defined by a wicking apparatus that is impregnated with fragrance oil. As air travels through the air column, particles of fragrance oil are transferred from the wicking apparatus into the air, ultimately being delivered into an airspace 302 outside of the fragrance delivery system 300. Fragrance delivery system 300 may be referred to as an dry air diffusion fragrance delivery system.

Fragrance delivery system 300 also includes a magnetic field generator incorporated within the same housing as the wicking apparatus. As illustrated in FIG. 3, the magnetic field generator generates a magnetic field 304 that extends into the airspace that is external to the fragrance delivery system 300. It will be appreciated that magnetic fields do not readily lend themselves to visual depiction and that, therefore, the magnetic field 304 shown in FIG. 3 is shown for illustrative purposes only and the magnetic fields generated by magnetic field generators described herein may have different orientations and extents than that shown in FIG. 3. For example, such magnetic fields may not have boundaries per se as suggested by FIG. 3, but rather may extend out into space.

FIG. 4 illustrates an example of how the magnetic field 304 generated by the magnetic field generator incorporated within the fragrance delivery system 300 may influence a particle of fragrance oil 400 after the particle of fragrance oil 400 has been delivered into the airspace 302. In particular, due to the properties of electricity and magnetism, the electronegative charge of the particle of fragrance oil 400, the velocity of the particle of fragrance oil 400, and the magnetic field yield a force on the particle of fragrance oil 400 that operates to influence the movement of the particle of fragrance oil 400 in the airspace 302 as illustrated, for example, in FIG. 4. As illustrated in FIG. 4, the force exerted on the particle of fragrance oil 400 influences the trajectory of the particle of fragrance oil 400 in the airspace 302, operating to suspend the particle of fragrance oil 400 in the airspace 302 longer than the particle of fragrance oil 400 otherwise might remain in the airspace 302 absent the magnetic field generated by the magnetic field generator. That is to say, the magnetic field generated by the magnetic field generator incorporated within the fragrance delivery system exerts a force on the particle of fragrance oil 400 that, at times, may act to reduce environmental forces (e.g., gravity) on the particle of fragrance oil 400, thereby increasing the length of time for which the particle of fragrance oil 400 remains suspended in the airspace 302.

Although FIGS. 3 and 4 illustrate a magnetic field generator incorporated within an dry air diffusion fragrance delivery system in order to suspend fragrant particles emitted by the fragrance delivery system in the air, it will be appreciated that such a magnetic field generator may be incorporated within any number of different types of fragrance delivery systems in order to suspend fragrant particles emitted by the fragrance delivery systems in the air.

As suggested above, in some implementations, the magnetic field generator may be a formed from a wound wire. As current flows through the windings of the wire, the movement of charge through the windings generates a magnetic field. Such a magnetic field generator may be referred to as a solenoid.

Figure 5A:
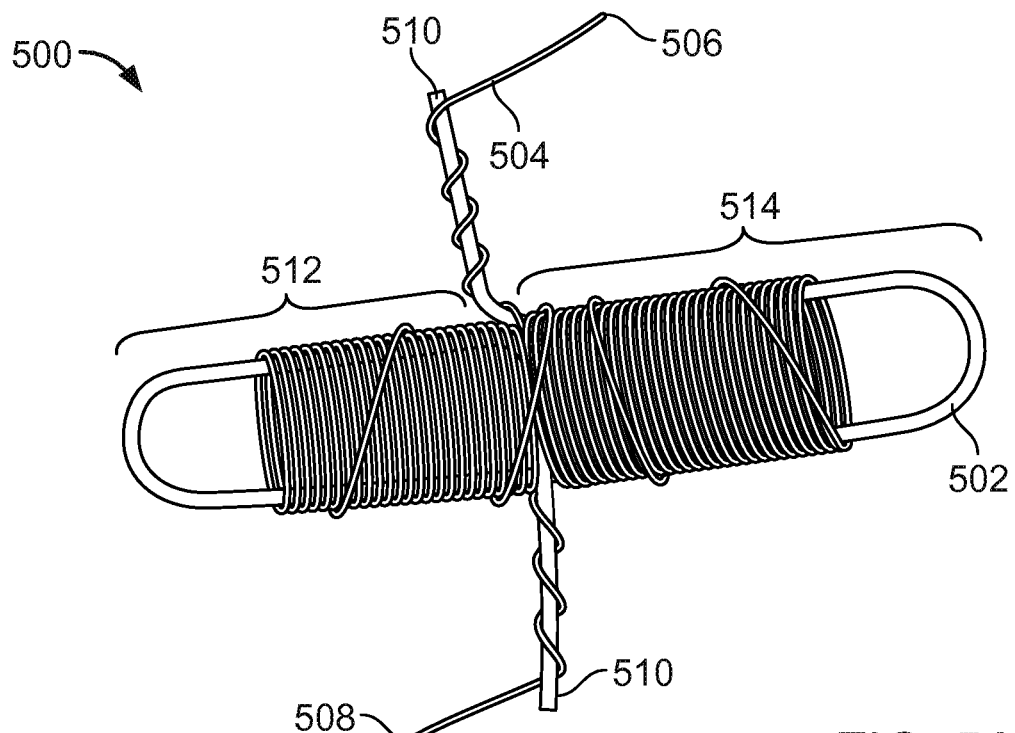
FIGS. 5A and 5B illustrate examples of a solenoid for use as a magnetic field generator to suspend particles of fragrant material in the air.

FIG. 5A is an illustration of a side view of one example of a solenoid 500 for use as a magnetic field generator to suspend particles of fragrant material in the air. As illustrated in FIG. 5A, solenoid 500 includes a core 502 around which a wire 504 is wrapped to form a coil. A first terminal 506 of wire 504 extends away from the core 502 and is connected to either a positive or negative terminal of a voltage source (not shown) while a second terminal 508 of wire 504 extends away from the core 502 and is connected to the other of the positive or negative terminal of the voltage source. Connecting terminals 506 and 508 of wire 504 to opposite terminals of the voltage source results in the flow of current through the wire, which generates a magnetic field both inside and outside of solenoid 500.

As illustrated in FIG. 5A, the core 502 of solenoid 500 is formed from a loop of metal, and a dividing post 510 serves to divide the core 502 into a first leg 512 and a second leg 514.

Figure 5B:
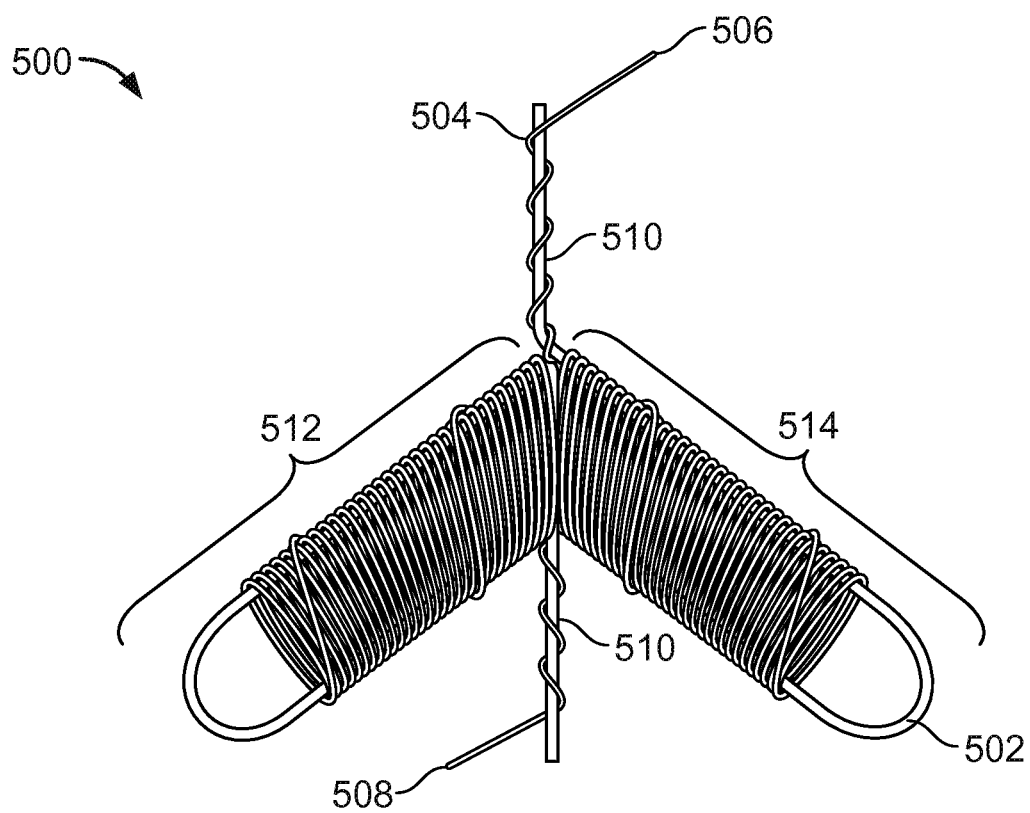

In some implementations, the first leg 512 and the second leg 514 may be positioned at substantially a 180° angle relative to one another. In alternative implementations, for example as illustrated in FIG. 5B, the first leg 512 and the second leg 514 of the core 502 may be bent around dividing post 510 such that the first leg 512 and the second leg 514 do not form a 180° angle relative to one another. The angle between the first leg 512 and the second leg 514 of the core 502 may influence the orientation and shape of the magnetic field generated by the solenoid 500. Therefore, the angle between the first leg 512 and the second leg 514 of the core 502 may be set depending upon the application and the dimensions of the space desired to be fragranced. Furthermore, in some implementations, the angle between the first leg 512 and the second leg 514 may be adjustable so that the orientation and shape of the magnetic field generated by the solenoid can be manipulated while the device is in operation.

As illustrated in FIGS. 5A and 5B, solenoid 500 includes a core 502 formed from a metal loop. As such, solenoid 500 includes a core that is conductive. However, in some implementations, a solenoid may include a core that is formed from a non-conductive material or the solenoid may not include an air core at all.

Figure 6A:
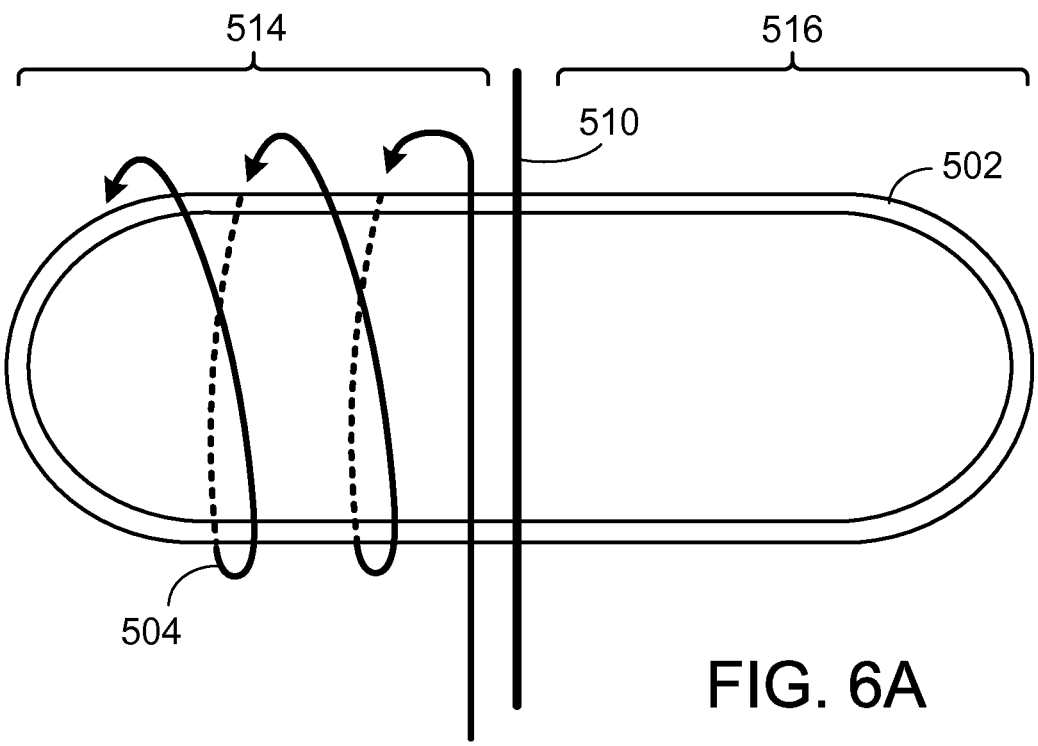
FIGS. 6A-6D illustrate an example of a technique for winding a wire around a core to form a solenoid.
Figure 6B:
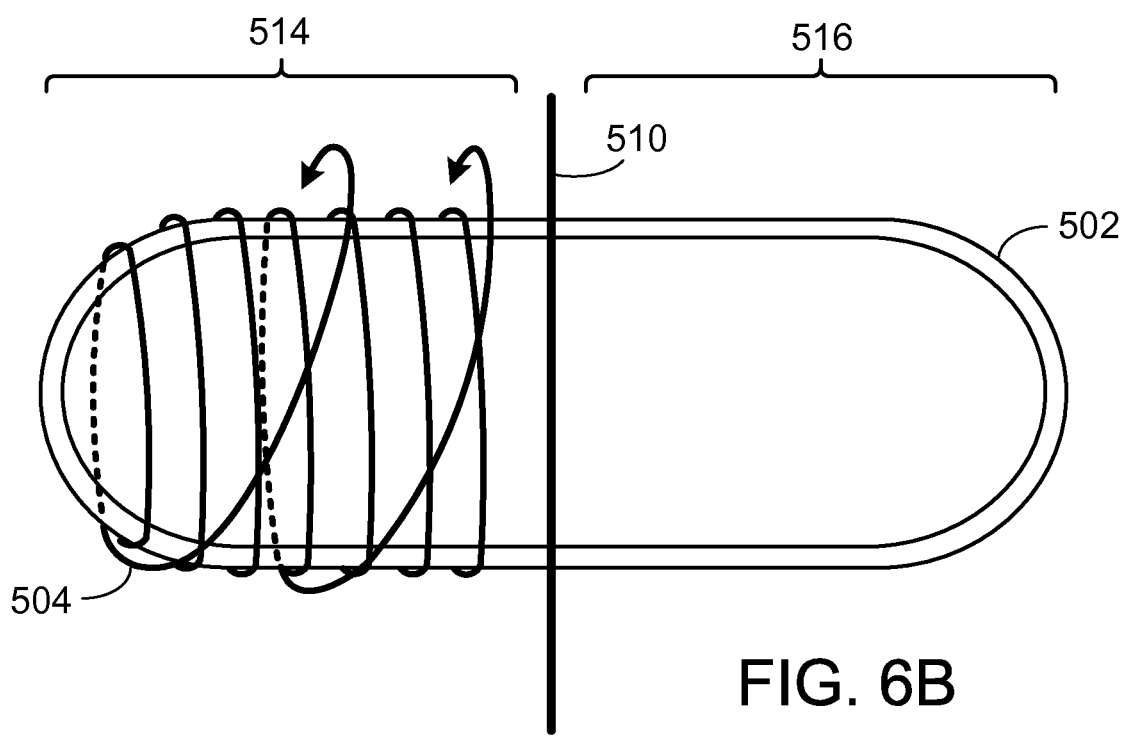
Figure 6C:
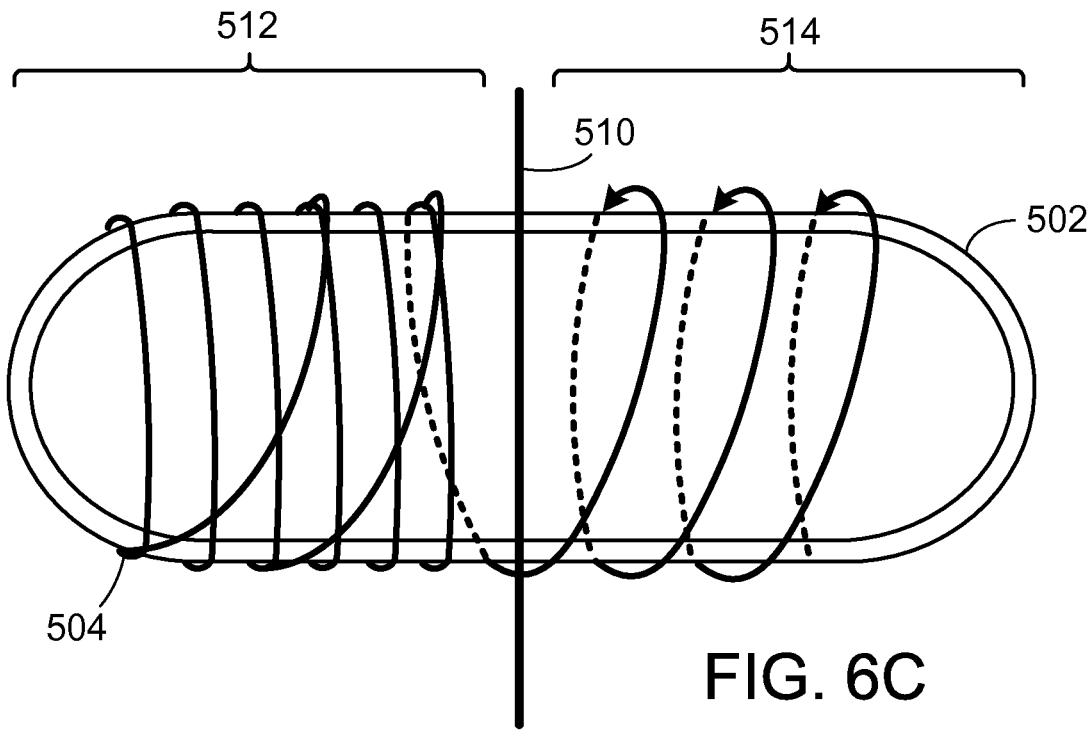
Figure 6D:
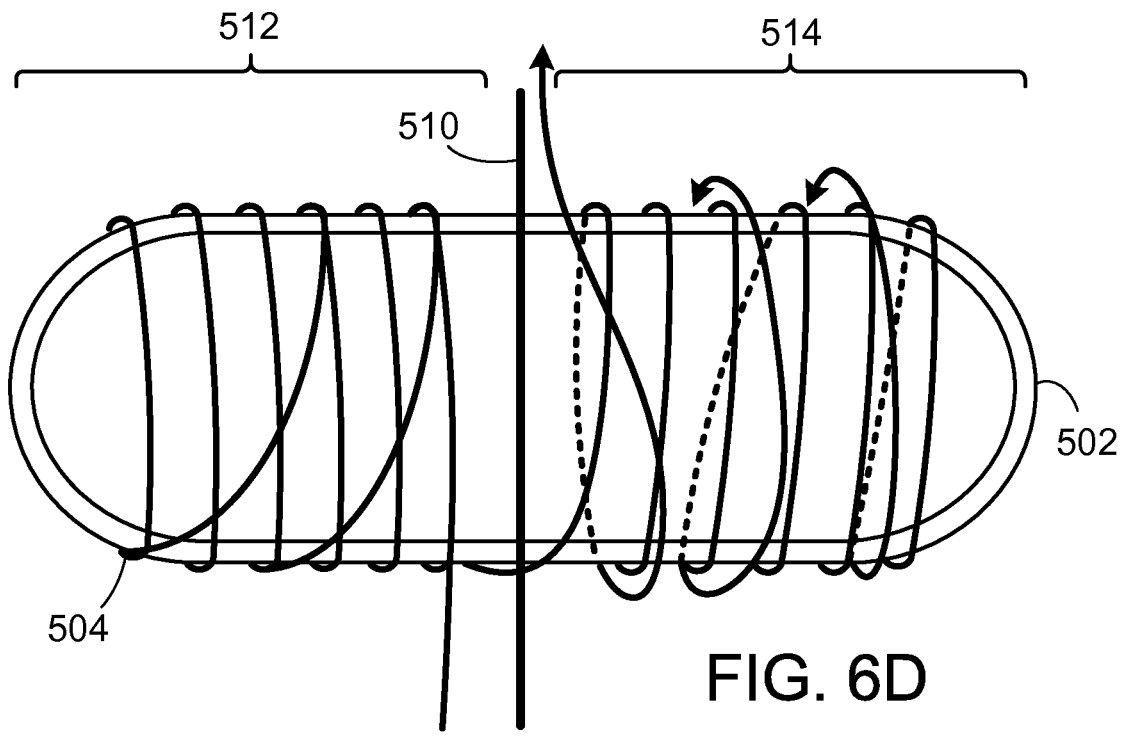
Figure 7A:
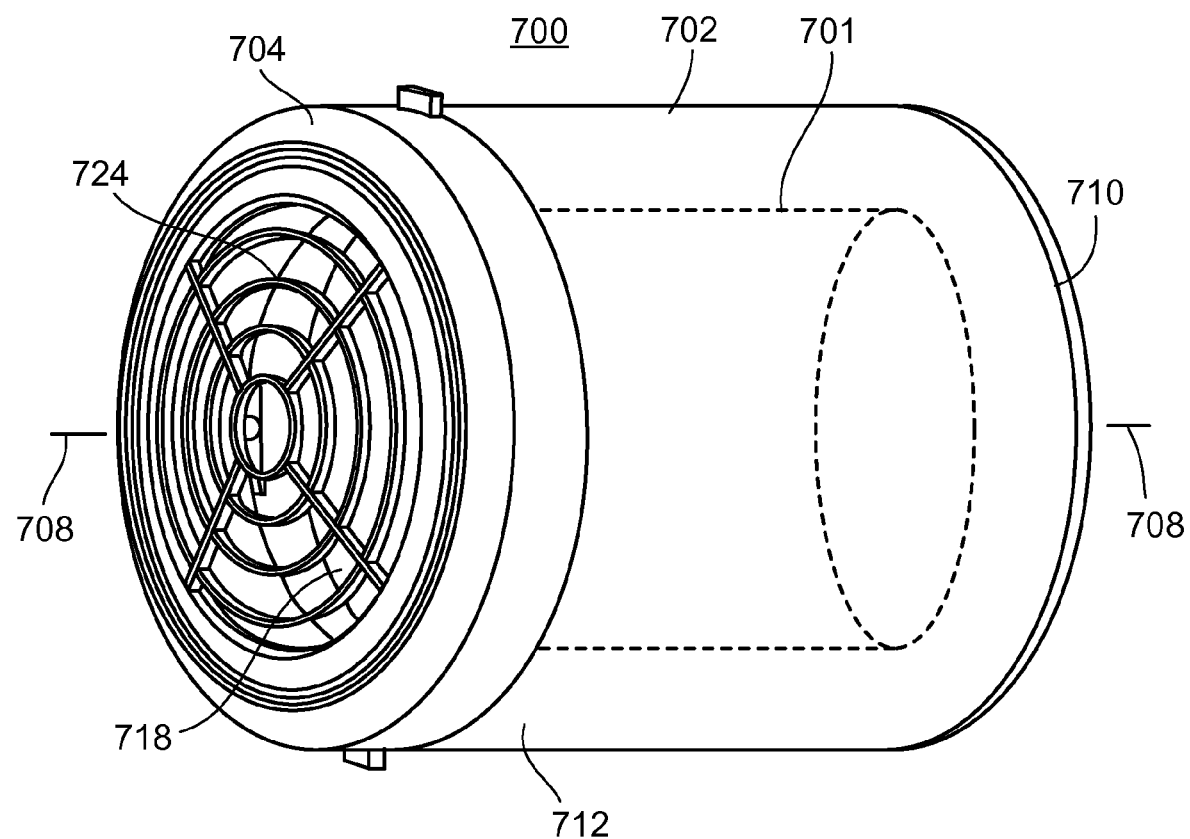
FIGS. 7A-7G depict an example of a dry air diffusion fragrance delivery system implemented in the form of a fragrance dispensing canister assembly that includes a wicking structure impregnated with a fragrance material and a magnetic field generator.
Figure 7B:
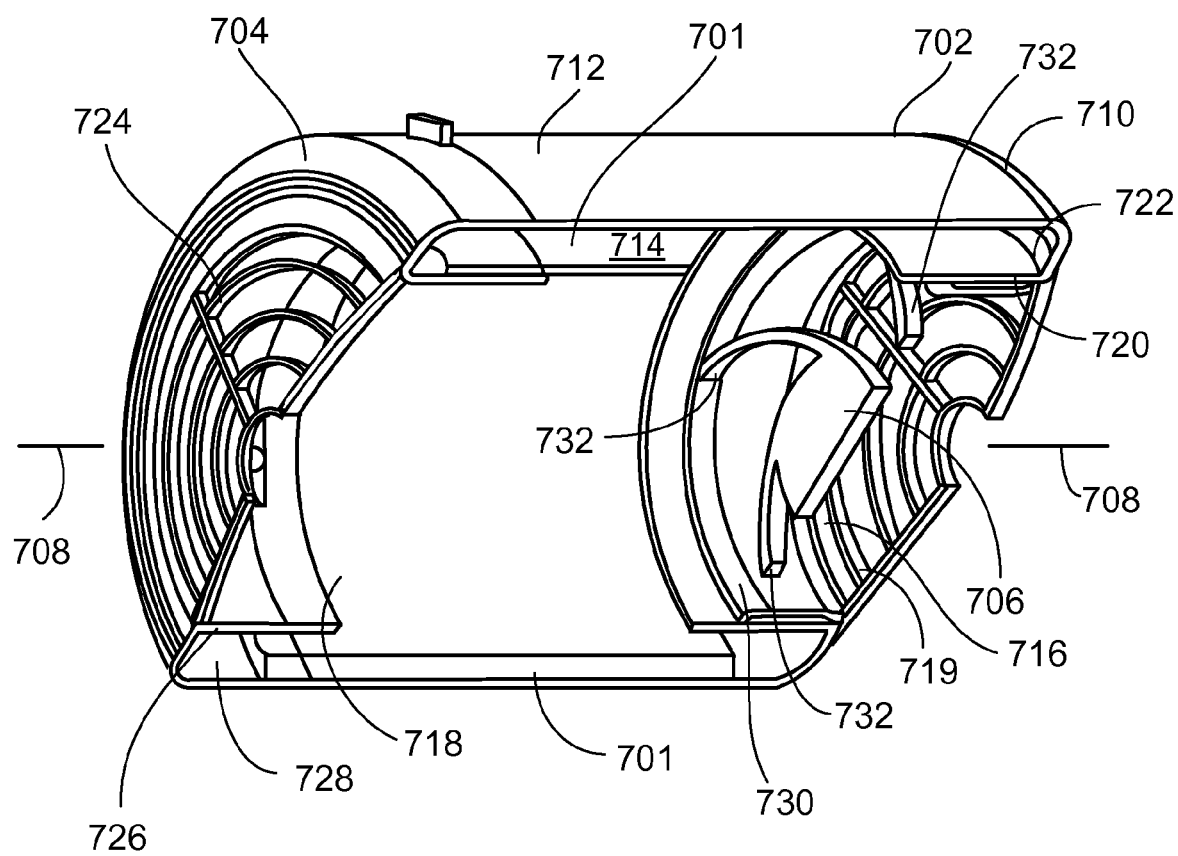
Figure 7C:
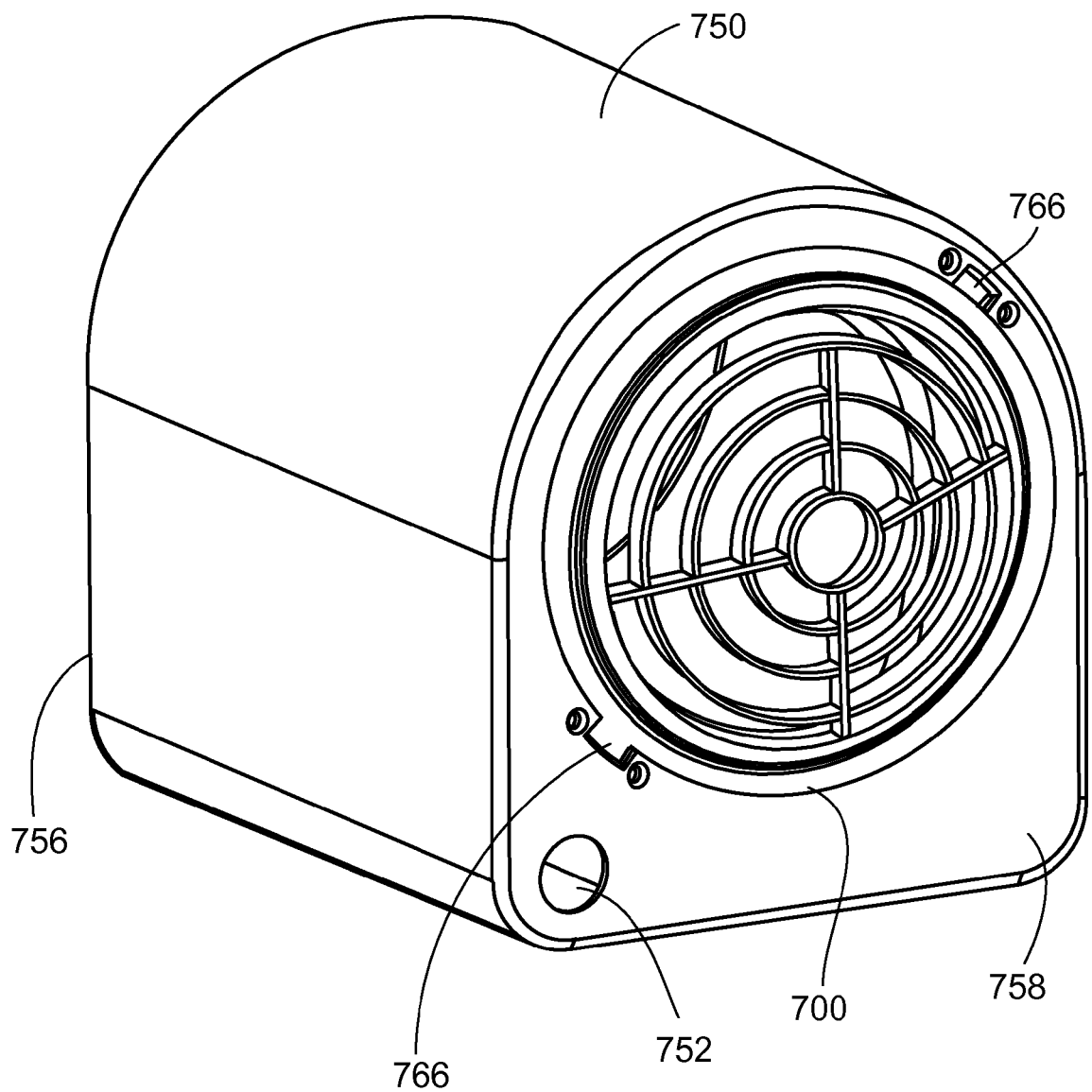
Figure 7D:
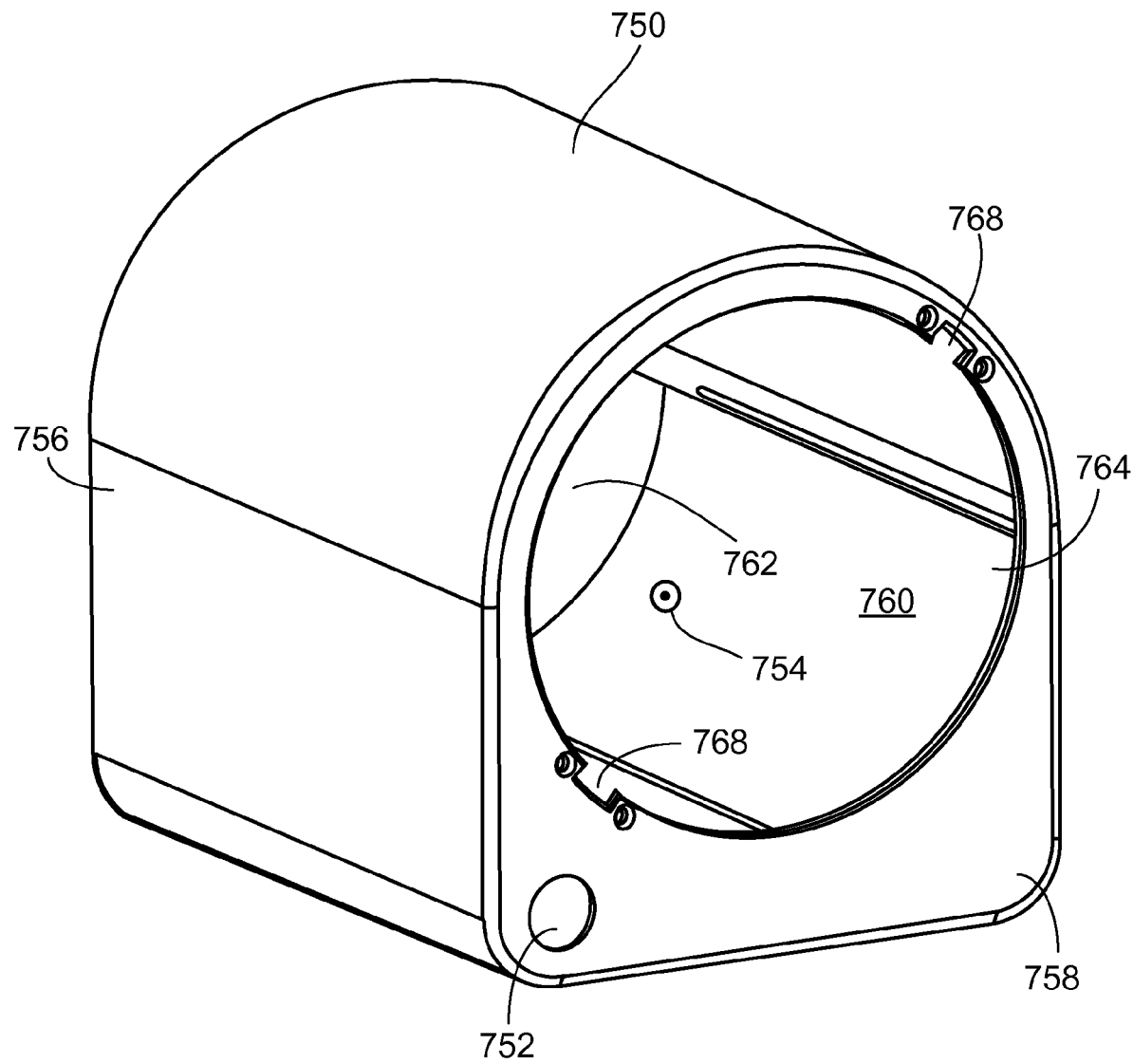
Figure 7E:
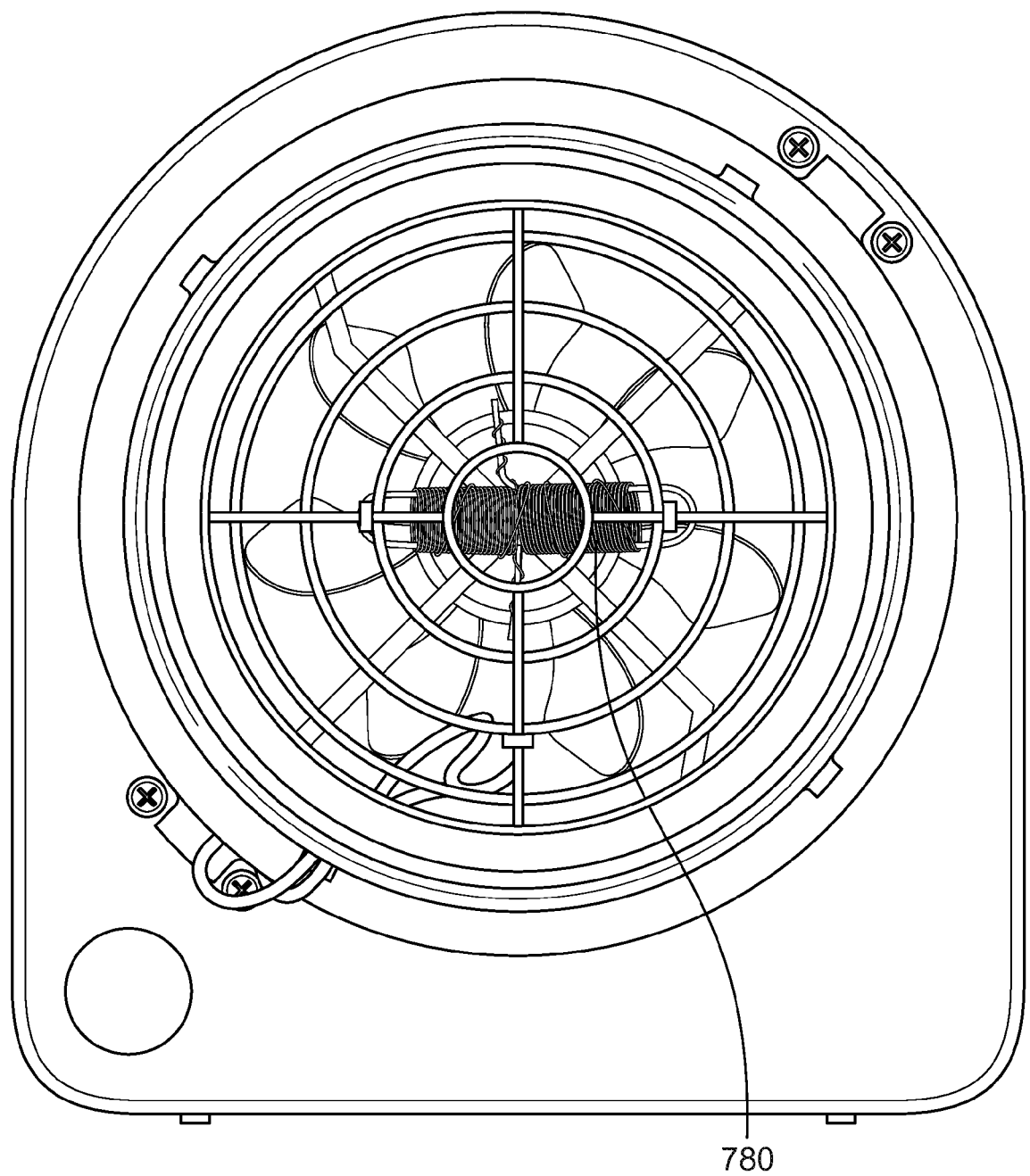
Figure 7F:
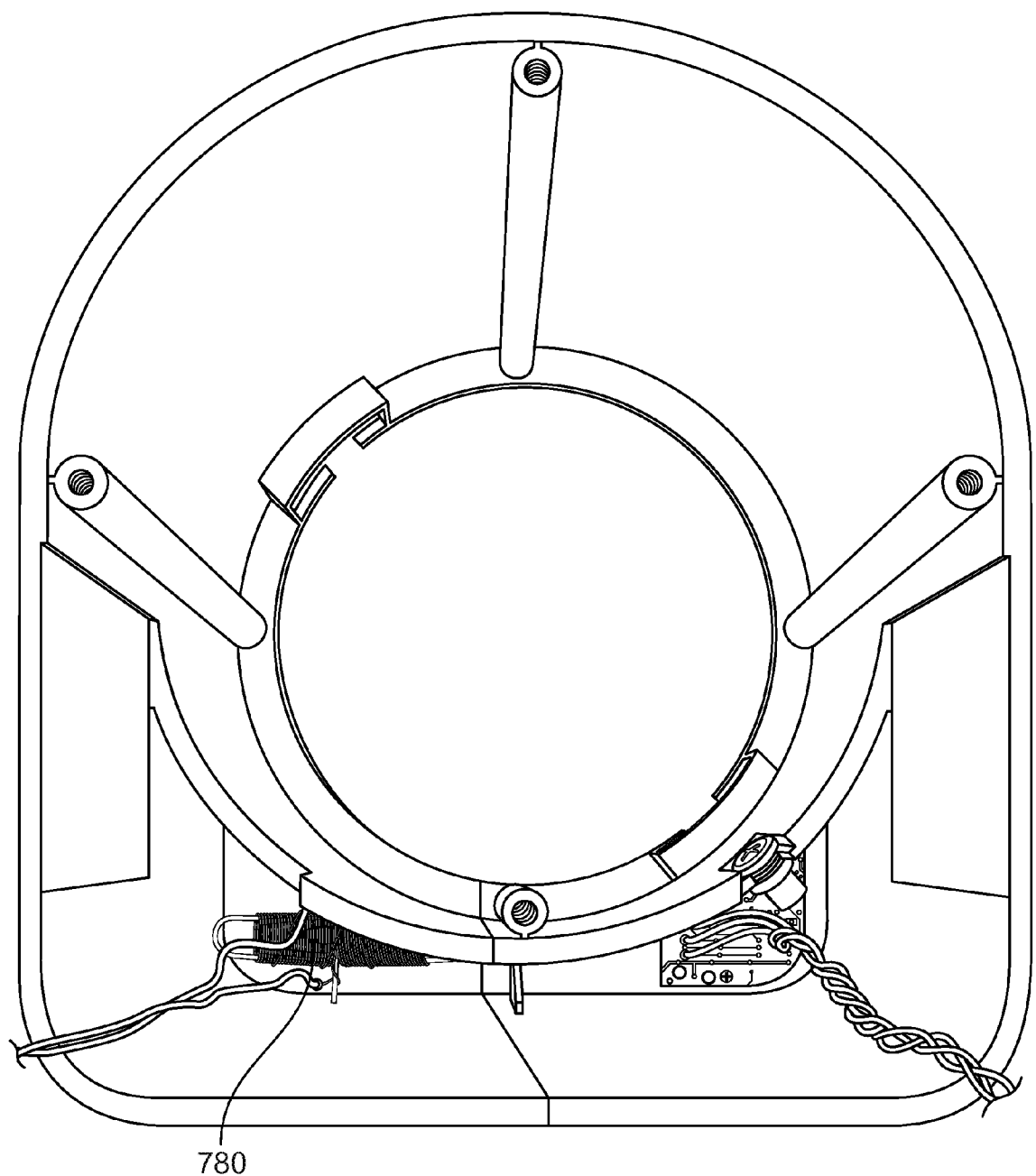
Figure 7G:
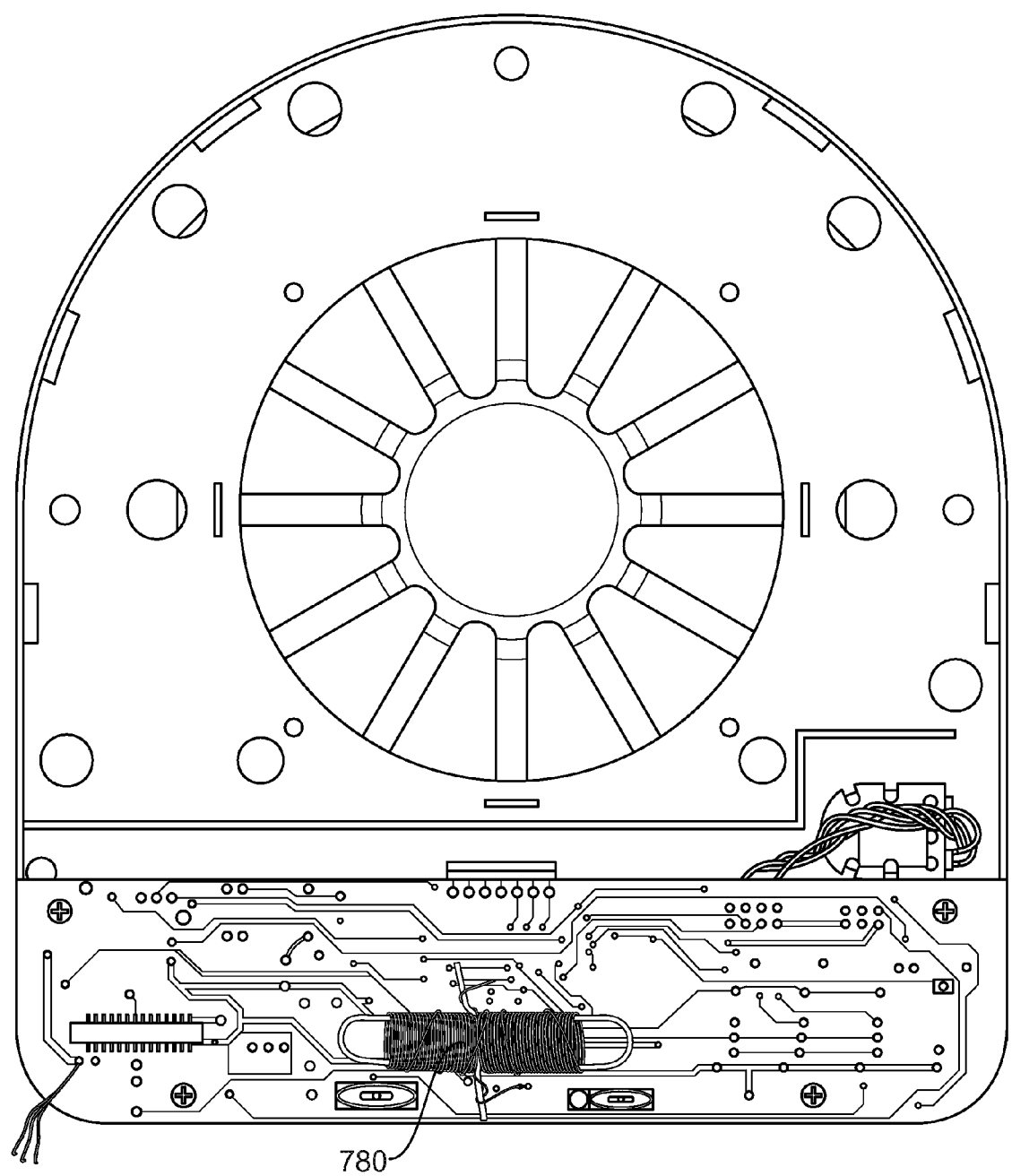

Various different techniques may be used to wind a wire around a core to form a solenoid as described herein. FIGS. 6A-6D illustrate an example of one technique for winding a wire around a core to form a solenoid. As illustrated in FIG. 6A, wire 504 may first be wound around first leg 512 of the core 502 starting near the dividing post 510. Wire 504 then may be wound around the first leg 512 of the core 502 such that the windings extend outwardly away from dividing post 510 to the terminal end of the first leg 512 of the core 502. Then, as illustrated in FIG. 6B, as the windings reach near to the terminal end of the first leg 512 of the core 502, the wire 504 may be wound around the first leg 512 of the core 502 such that the windings begin to extend inwardly, back toward dividing post 510. As illustrated in FIG. 6C, upon returning to dividing post 510, wire 504 may be wound such that it crosses over dividing post 510 and the windings extend outwardly toward the terminal end of the second leg 514 of the core 502. Thereafter, as illustrated in FIG. 6D, when the windings near the terminal end of the second leg 514 of the core 502, the wire may be wound around the second leg 514 of the core 502 such that the windings begin to extend inwardly, back toward dividing post 510.

In some implementations, the number of windings on the first leg 512 of the core 502 may be equal to the number of windings on the second leg 514 of the core 502, while, in alternative implementations, the number of windings on the first leg 512 of the core 502 may be different than the number of windings on the second leg 514 of the core 502. Furthermore, in some implementations, the number of windings along the first leg 512 of the core 502 that extend outward from dividing post 510 may be significantly greater than the number of windings along the first leg 512 of the core 502 that extend inward toward dividing post 510. Similarly, in some implementations, the number of windings along the first leg 514 of the core 502 that extend outward from dividing post 510 may be significantly greater than the number of windings along the second leg 514 of the core 502 that extend inward toward dividing post 510.

As described above, a magnetic field generator may be used in conjunction with many different types of fragrance delivery systems in order to suspend fragrant particles emitted by the fragrance delivery systems in the air.

For example, in some implementations, a magnetic field generator may be used in conjunction with a dry air diffusion fragrance delivery system to suspend particles of fragrant oil delivered by the dry air diffusion fragrance delivery system in the air after they are delivered.

Referring to FIGS. 7A and 7B, a dry air diffusion fragrance delivery system may be implemented in the form of a fragrance dispensing canister assembly 700 (e.g., a cartridge) that includes a wicking structure 701 impregnated with a fragrance material (e.g., a fragrance oil), a canister body 702, a nose cone 704 (e.g., a lid), and a fan 706. The canister body 702 is configured in the form of a hollow cylinder about an axis 708 and has an air intake end 710 and an air output end 712. The hollow canister body 702 defines a canister interior 714, an air intake aperture 716 located at the air intake end 710 of the canister body 702, and an air output aperture 718 located at the air output end 712 of the canister body 702. The canister body 702 further includes circular grill slats 719 covering the air intake aperture 716. Other configurations also may be used to cover the air intake aperture 716. For example, a mesh grill or louvers may be used to cover the air intake aperture 716. Alternatively, the air intake aperture 716 may be uncovered.

The wicking structure 701 is received within the canister interior 714 such that the wicking structure 701 and the canister body 702 form substantially concentric cylinders. As a result, air may enter the canister interior 714 through the air intake aperture 716, flow through the air channel of the wicking structure 701, and exit the canister interior 714 through the air output aperture 718.

The canister body 702 is further configured to form a lip 720 at the air intake end 710 that wraps around the wicking structure 701. The lip 720 may serve to hold the wicking structure 701 in place within the canister interior 714. Additionally or alternatively, the lip 720 may prevent fragrance material from leaking out of the canister assembly 700 through the air intake aperture 716 by forming a well 722 for collecting fragrance material that leaks from the wicking structure assembly 701. The canister body 702 may be composed of various different materials including, for example, plastic, metal, polyester film, or a combination thereof.

The nose cone 704 is coupled to the air output end 712 of the canister body 702. As illustrated, the nose cone 704 includes circular grill slats 724. The circular grill slats 724 may help to regulate or direct airflow through the air output aperture 718. Other mechanisms also may be used to help regulate or direct airflow through the air output aperture 718. For example, a mesh grill or louvers may be used to regulate airflow through the air output aperture 718.

The nose cone 704 is configured to form a lip 726 that wraps around the wicking structure 701 in the vicinity of the air output end 712 of the canister body 702. The lip 726 may also serve to hold the wicking structure assembly 701 in place within the canister interior 714. Additionally or alternatively, the lip 726 may prevent fragrance material from leaking out of the canister assembly 700 through the air output aperture 718 by forming a well 728 for collecting fragrance material that leaks from the wicking structure assembly 701.

The fan 706 includes a fan housing 730 and fan blades 732 and is coupled to the canister body 702 in the vicinity of the air intake end 710. The fan 706 is configured to encourage airflow through the air channel and to project air out of the canister assembly 700. During operation, the fan 706 forces airflow through the air channel by drawing air into the air channel through the air intake aperture 716 and propelling air out of the air channel through the air output aperture 718.

The fan blades 732 are aligned substantially with the inner surface of the wicking structure 701. Stated differently, the fan blades 732 and the air channel are configured to have substantially the same dimensions. Configuring the fan blades 732 such that they are of substantially the same dimension as the air channel may increase the efficiency of the fan 706 as substantially all of the airflow generated by the fan may be corralled within the air channel thereby eliminating, or at least reducing, blow-by. Configuring the fan blades 732 such that they are of substantially the same dimension as the air channel also may limit the amount of noise generated by the fan 706 during operation.

As air flows through the air channel, fragrance molecules evaporate from the surface of the wicking structure 701 into the air. Thereafter, when the air leaves the air channel, the fragrance molecules are delivered into the airspace.

Using the fan 706 to force airflow through the air channel helps to increase the rate of evaporation of fragrance molecules from the wicking structure 701. In general, as the velocity of the airflow through the air channel increases, the evaporation rate of the fragrance molecules also increases. Additionally, using the fan 706 to propel air out of the air channel helps the canister assembly 700 to disperse fragrance molecules across a larger volume than otherwise would occur.

Referring to FIGS. 7C and 7D, the fragrance dispensing canister assembly 700 is housed in a canister housing 750 having a motion sensor 752 and an electrical outlet 754 for providing power to the fan 706 of the canister assembly 700 and/or a magnetic field generator. The canister housing 750 also includes a housing intake end 756 and a housing output end 758. In addition, the canister housing 750 defines a canister cavity 760 configured to receive the canister assembly 700, a housing intake aperture 762 leading to the canister cavity 760 at the housing intake end 756, and a housing output aperture 764 leading to the canister cavity 760 at the housing output end 758. The canister assembly 700 is received within the canister cavity 760 with the air intake end 710 of the canister body 702 positioned in the vicinity of the housing intake end 756 and the air output end 712 of the canister body 702 positioned in the vicinity of the housing output end 758.

The canister housing 750 may be equipped with a power supply capable of supplying power, such as a battery assembly. Additionally or alternatively, the canister housing 750 may be equipped to receive power from an external source.

The canister housing 750 may be configured to regulate the power (e.g., voltage or current) supplied to the fan and/or the magnetic generator (not shown), thereby allowing the fan speed and/or the strength of the magnetic field generated by the magnetic generator to be controlled. In some implementations, the canister housing 750 includes controls for manually setting (e.g., selecting or controlling) the fan speed and/or controls for manually setting the strength of the magnetic field generated by the magnetic field generator. Manually setting the fan speed enables a person to adjust the amount of fragrance dispensed. For example, selecting a higher fan speed causes more air to flow through the canister, which results in more fragrance being dispensed. In contrast, selecting a lower fan speed or turning off the fan causes less air to flow through the canister (as compared with a higher fan speed), which results in less fragrance being dispensed. Manually setting the strength of the magnetic field generated by the magnetic generator enables a person to control fragrant particles delivered into an airspace.

The motion sensor 752 may be configured to detect motion up to a predetermined distance, such as twenty feet away from the motion sensor 752.

The power supplied to the fan 706 and/or the magnetic field generator also may be controlled at least in part by the motion sensor 752. Consequently, the operation of the fan 706 and/or the magnetic field generator also may be controlled by the motion sensor 752. For example, power may be supplied to the fan 706 and/or the magnetic field generator when the motion sensor 752 detects motion within the vicinity of the canister housing 750. The canister housing 750 also may include a timing circuit for regulating the power provided to the fan 706 and/or magnetic field generator. The timing circuit may control the power provided to the fan 706 such that the fan 706 is cycled on and off and/or the timing circuit may control the power provided to the fan magnetic field generator such that the magnetic field generator is cycled on and/off. For example, one or both of the fan 706 and the magnetic field generator may be cycled on for 30 seconds and off for 30 seconds. The period of the cycle may be variable. The timing circuit also may be configured to operate in conjunction with the motion sensor 752. For example, the timing circuit may be triggered to provide power to the fan 706 and/or magnetic field generator in response to the detection of motion by the motion sensor 752. The timing circuit then may cut off the supply of power to the fan 706 and/or the magnetic field generator after a defined period of time has elapsed since the detection of motion.

As such, the canister housing 750 is operable to deliver and suspend fragrance when the motion sensor 752 is triggered and may be referred to as a sensing fragrance apparatus. Thus, a sensing fragrance apparatus provides for the delivery of fragrance when a person is believed to be present in an environment, such as when motion is detected. In this way, a sensing fragrance apparatus may provide the effect of a continuous fragrance dispensing system when people are present in the environment, while saving on the amount of fragrance oil and energy otherwise consumed.

A magnetic field generator may be incorporated at various different locations within the fragrance dispensing canister assembly 700 and/or the canister housing 750 of the dry air diffusion fragrance delivery system described above in connection with FIGS. 7A-7D in order to suspend fragrant particles delivered by the fragrance delivery apparatus in the air.

For example, as illustrated in FIG. 7E, a magnetic field generator 780 may be secured to the nose cone 704 of the canister assembly 700. Additionally or alternatively, a magnetic field generator 780 may be secured to an interior wall at the housing output end 758 of the canister housing 750 beneath the canister cavity 760 defined in the canister housing 750, as illustrated in FIG. 7F, and/or a magnetic field generator 780 may be secured to a circuit board 782 coupled to an interior wall at the housing intake end 756 of the canister housing 750, as illustrated in FIG. 7G.

The location of the magnetic field generator 780 within the fragrance dispensing canister assembly 700 may influence the strength and/or orientation of the magnetic field in the airspace surrounding the fragrance dispensing canister assembly 700. For instance, if the magnetic field generator 780 if there is little to no structure concealing the magnetic field generator 780 from the airspace (e.g., as illustrated in FIG. 7E), the strength of the magnetic field in the airspace may be stronger than if there is more structure between the magnetic field generator 780 and the airspace (e.g., as illustrated in FIGS. 7F and 7G).

In addition to incorporating a magnetic field generator within a dry air diffusion fragrance delivery system or otherwise using a magnetic field generator in conjunction with a dry air diffusion fragrance delivery system to suspend delivered fragrant particles in the air, as discussed above in connection with FIGS. 7A-7G, a magnetic field generator also can be incorporated within or otherwise used in conjunction with any other type of fragrance delivery system in order to suspend delivered fragrant particles in the air.

For example, FIG. 8A is an illustration of a evaporative fragrance delivery system 800, within which a magnetic field generator 802 is incorporated in order to suspend fragrance particles delivered by the evaporative fragrance delivery system 800 in the air 804. In particular, evaporative fragrance delivery system 800 includes a base 806 configured to hold a delivery stick 808 such that the delivery stick extends away from base 806 into the air 804. In some implementations, the base 806 may be configured to hold delivery stick 808 substantially upright, whereas, in other implementations, base 806 may be configured to hold delivery stick 808 at a less than upright angle. Delivery stick 808 is coated with a fragrant material that, over time, evaporates from the delivery stick 808 and is delivered into the air 804.

For the purposes of illustration, a portion of the base 806 of evaporative fragrance delivery system 800 has been cut away from the figure to reveal that a magnetic field generator 802 (e.g., a solenoid) is incorporated within the base 806 in order to suspend fragrant material released by evaporative fragrance delivery system 800 in the air 804. As illustrated in FIG. 8A, first and second terminals 810 and 812 of magnetic field generator 802 are connected to opposite terminals of a power source 814 such that current flows through magnetic field generator 802, thereby creating a magnetic field that serves to suspend fragrance particles delivered by the evaporative fragrance delivery system 800 in the air. As illustrated power source 814 may receive power from an external power supply (e.g., a wall socket) and supply power to components of the evaporative fragrance delivery system 800 and/or power source 814 may include a battery which is used to supply power to components of the evaporative fragrance delivery system 800.

Figure 8A:
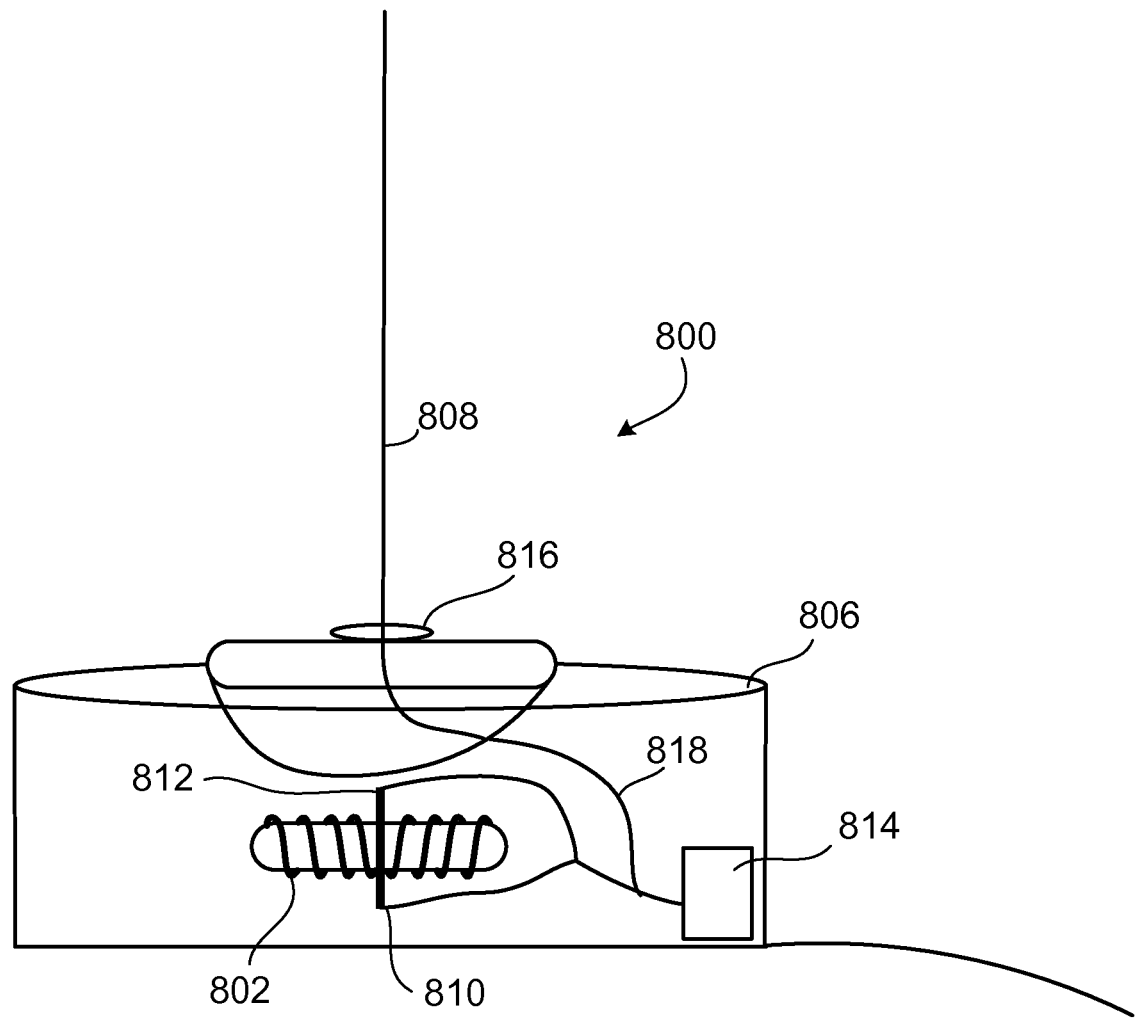
FIGS. 8A-8C depict examples of a evaporative fragrance delivery system, within which a magnetic field generator is incorporated in order to suspend fragrance particles delivered by the evaporative fragrance delivery system in the air.

In some implementations, base 806 may hold delivery stick 808 in a conductive socket which is electrically coupled to a negative terminal of a power source. For example, as illustrated in FIG. 8A, base 806 holds delivery stick 808 in a conductive socket 816 which is electrically coupled to power source 814 by wire 818. In particular, one terminal of wire 818 is electrically coupled to conductive socket 816 and another terminal of wire 818 is electrically coupled to the negative terminal of power source 814. As a result, a negative electrical bias is applied to delivery stick 808 which may serve to increase the negativity of the fragrance molecules coated on delivery stick 808.

Figure 8B:
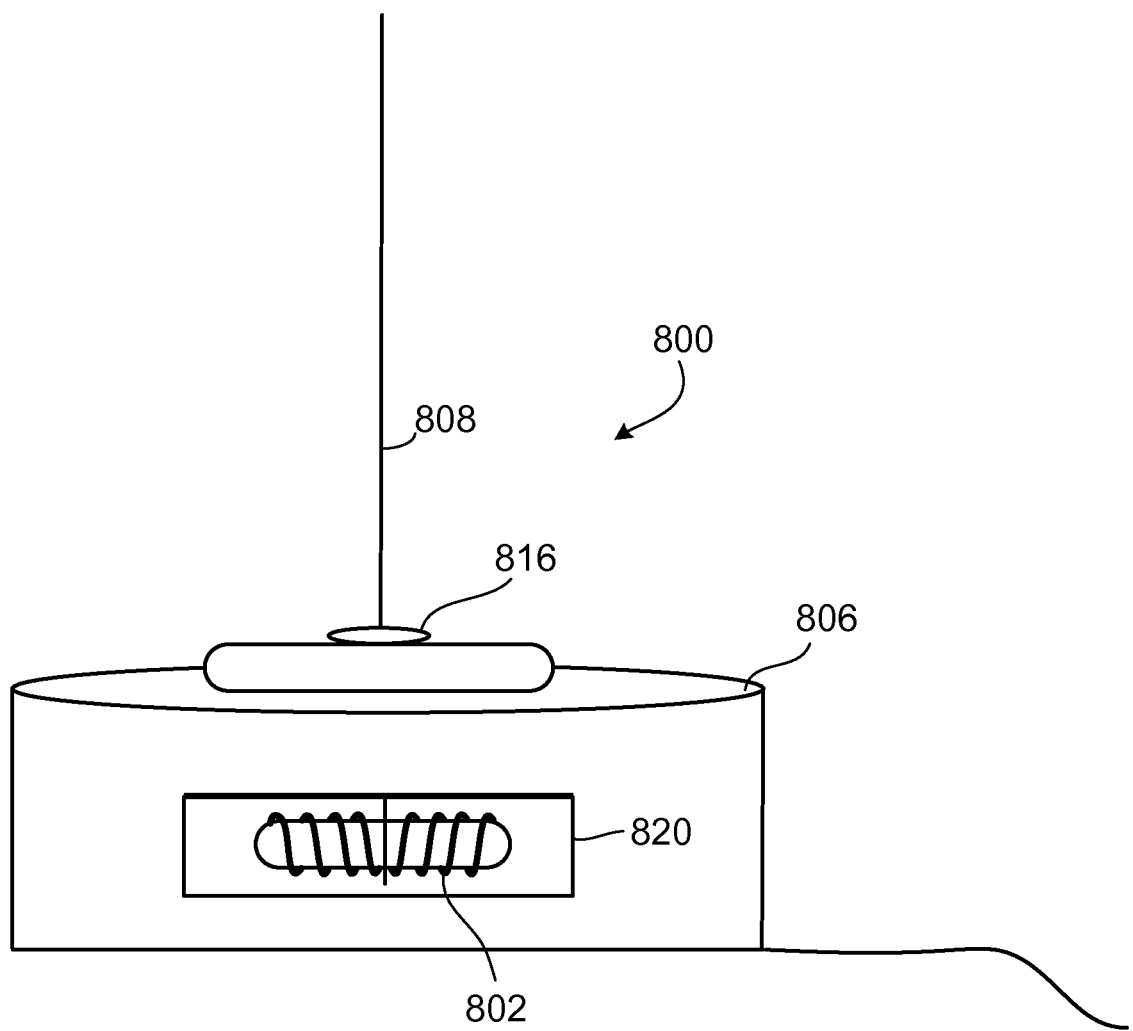
Figure 8C:
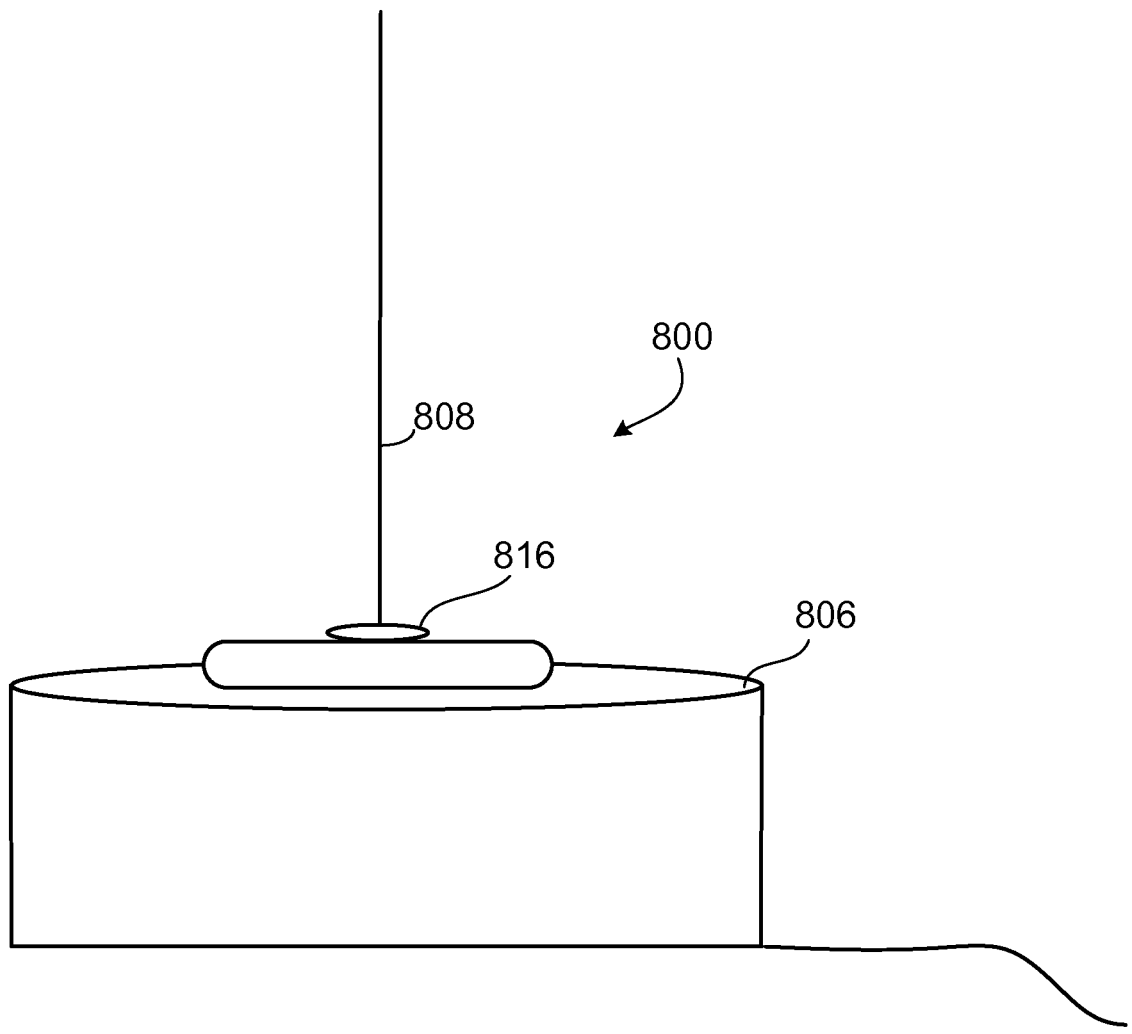

Referring to FIG. 8B, in some implementations, a slot 820 may be formed in base 806 of evaporative fragrance delivery system 800 in order to expose magnetic field generator 802. Alternatively, referring to FIG. 8C, in some other implementations, no slot may be formed in base 806 of evaporative fragrance delivery system 800 and magnetic field generator 802 may be completely enclosed within base 806.

A magnetic field generator also may be incorporated within or otherwise used in conjunction with an atomized fragrance delivery system that atomizes a fragrance oil (or other liquid) into a fine mist that is delivered into an airspace.

Figure 9A:
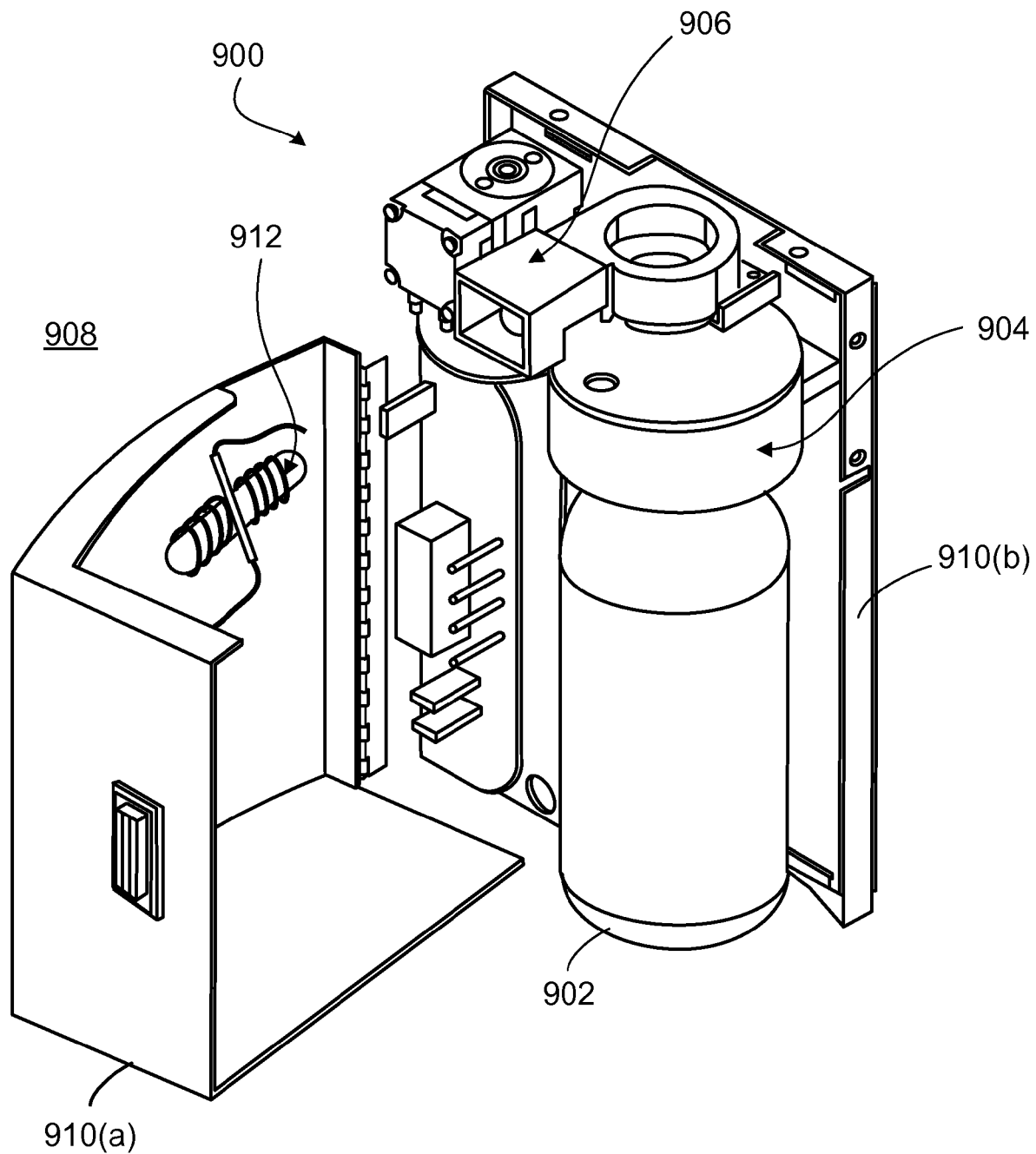
FIGS. 9A and 9B depict of an example of an atomized fragrance delivery system.

For example, FIG. 9A is an exploded view of an atomized fragrance delivery system 900. As illustrated in FIG. 9A, atomized fragrance delivery system 900 includes a reservoir 902 for holding a fragrance oil, an atomizer assembly 904 for atomizing the fragrance oil held within reservoir 902, and a nozzle 906 for delivering the atomized fragrance oil into the air 908 as a fine mist. In addition, the atomized fragrance delivery system 900 also includes a housing 910 having a front portion 910(*a*) and a back portion 910(*b*) for encasing, among other elements, the reservoir 902 and the atomizer assembly 904. Nozzle 906 remains exposed so as to enable the delivery of the atomized fragrance oil into the air 908. As illustrated in FIG. 9A, a magnetic field generator 912 is secured to an interior wall of the front portion 910(*a*) of the housing 910 for the atomized fragrance delivery system 900. This magnetic field generator 912 may be used to generate a magnetic field within the vicinity of the atomized fragrance delivery system 900 such that at least some of the fragrance particles emitted by the atomized fragrance delivery system 900 enter the magnetic field generated by the magnetic field generator 912 and are influenced by the force exerted on them by the magnetic field as a consequence.

Figure 9B:
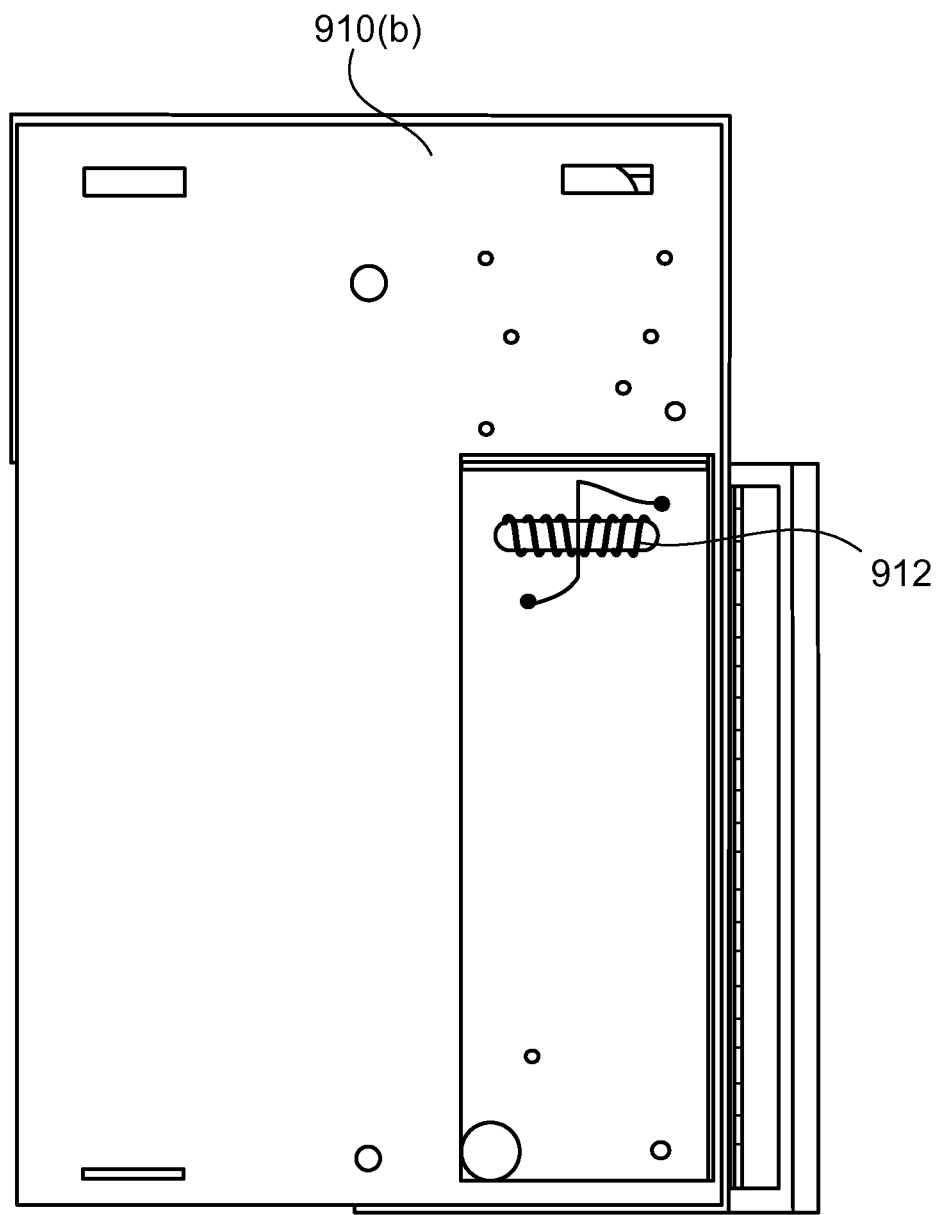

Magnetic field generator 912 can be located in one or more additional or alternative locations when incorporated within or otherwise used in conjunction with an atomized fragrance delivery system such as the atomized fragrance delivery system 900 illustrated in FIG. 9A. For example, as illustrated in FIG. 9B, a magnetic field generator 912 may be secured to an exterior wall of the back portion 910(*b*) of the housing 910 for the atomized fragrance delivery system 900.

In some implementations, multiple different magnetic field generators may be used in conjunction with a fragrance delivery system into order to control the areas into which the released fragrance travels. For example, when a fragrance delivery system is deployed in a building having different rooms and hallways, multiple different magnetic field generators may be used in conjunction with the fragrance delivery system to control the distribution of the fragrance released by the fragrance delivery system throughout different rooms and hallways within the building.

The apparatus may have multiple additional magnetic field generators, each of which is configured to generate an additional magnetic field, that may be physically distinct from the magnetic field generator and other of the multiple additional magnetic field generators, and may be displaced from other of the multiple additional magnetic field generators. In some implementations, the magnetic field generator and the multiple additional magnetic field generators can be configured to generate magnetic fields that are oriented such that at least some of the fragrant particles released into the magnetic field generated by the magnetic field generator are transferred to each of the additional magnetic fields. In these implementations, multiple solenoids positioned throughout the building may be used to enhance the dispersal of the fragrance.

Figure 10:
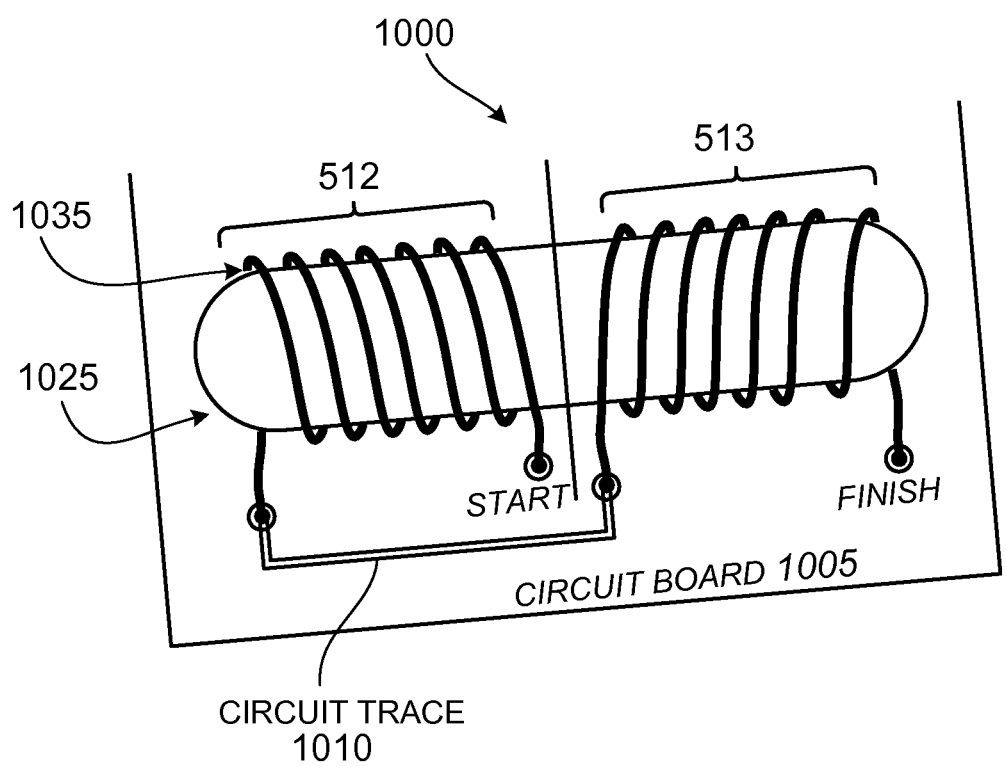
FIG. 10 depicts an example of a solenoid implementation that includes a magnetic field generator with a circuit board.

FIG. 10 shows an implementation that includes a magnetic field generator with a circuit board. A wire 1035 is wrapped around a core 1025 of the solenoid 1000, where a circuit trace 1010 on a circuit board 1005 connects the first leg 512 and second leg 513. In this implementation, a magnetic field generator is formed where the circuit trace 1010 on the circuit board 1005 is used instead of a continuous wire between the legs 512, 513.

A number of implementations have been described. Nevertheless, it will be understood that various modifications may be made. For example, a magnetic field generator may be used in conjunction with a liquid electric fragrance delivery system (e.g., a plug-in) to suspend fragrance particles delivered by the liquid electric fragrance delivery system into an airspace within the air. In such implementations, the magnetic field generator may be incorporated within the same housing as the liquid electric fragrance delivery system, or, alternatively, the magnetic field generated may be physically distinct and displaced from the liquid electric fragrance delivery system. A magnetic field generator also may be incorporated within or used in conjunction with all other forms of fragrance delivery systems including, for example, piezo-electric fragrance delivery systems, electrostatic fragrance delivery systems, ultrasonic fragrance delivery systems, nebulization fragrance delivery systems, candles, and reed diffusers.

Furthermore, in some implementations, multiple magnetic field generators may be incorporated within the same housing as a scent delivery system. In such implementations, the magnetic field generators may be stacked on top of one another and/or disposed adjacent to one another such that the magnetic fields created by the magnetic field generators are additive.

Although only a few implementations have been described in detail above, other implementations are possible. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a combination can in some cases be excised from the combination, and the combination may be directed to a subcombination or variation of a subcombination. It should be appreciated that disclosed implementations may encompass equivalents and substitutes for one or more of the example techniques described herein. The present specification describes specific examples to accomplish a more general goal in another way. This description should be understood to represent example implementations and the claims following are intended to cover any equivalent, modification or alternative. Accordingly, other implementations are within the scope of the following claims.

What is claimed is:

1. An apparatus for fragrancing an air space comprising:
a magnetic field generator that includes a conductive coil and is configured to generate a magnetic field; and
a fragrance delivery system configured to release fragrant particles into an air space such that at least some of the fragrant particles enter the magnetic field generated by the magnetic field generator,
wherein the magnetic field generator also is configured to influence fragrant particles entering the magnetic field via the magnetic field upon completion of the release of the fragrant particles into the air space.

2. The apparatus of claim 1 further comprising a voltage source having a positive terminal and a negative terminal wherein the positive terminal of the voltage source is connected to a first terminal of the conductive coil and the negative terminal of the voltage source is connected to a second terminal of the conductive coil such that an electric current flows through the conductive coil between the first terminal and the second terminal thereby generating the magnetic field.

3. The apparatus of claim 1 wherein:
the magnetic field generator further includes a core, and
the conductive coil is wound around the core.

4. The apparatus of claim 3 wherein the core is formed from a conductive material.

5. The apparatus of claim 3 wherein the core is formed from a non-conductive material.

6. The apparatus of claim 3 wherein:
the core includes a first leg and a second leg that is mechanically coupled to the first leg,
at least one winding of the conductive coil is wound around the first leg of the core, and
at least one winding of the conductive coil is wound around the second leg of the core.

7. The apparatus of claim 6 wherein:
the first leg of the core and the second leg of the core are formed from a contiguous piece of material,
the core includes a dividing post that bisects the contiguous piece of material thereby defining the first and second legs of the core,
the conductive coil is formed from a wire, the wire having a first end and a second end, and
from the perspective of the first end of the wire, the wire is wound around the first leg of the core before the wire is wound around the second leg of the core, with windings around the first leg of the core beginning adjacent to the dividing post and extending generally outwardly along the first leg of the core away from the dividing post and the second leg of the core before returning inwardly along the first leg of the core towards the dividing post and the second leg of the core and windings around the second leg of the core beginning adjacent to the dividing post and extending generally outwardly along the second leg of the core away from the dividing post and the first leg of the core before returning inwardly along the second leg of the core towards the dividing post and the first leg of the core.

8. The apparatus of claim 7 further comprising a voltage source having a positive terminal and a negative terminal, wherein:
the first end of the wire is electrically coupled to the negative terminal of the voltage source, and
the second end of the wire is electrically coupled to the positive terminal of the voltage source.

9. The apparatus of claim 7 wherein a number of windings around the first leg of the core is equal to a number of windings around the second leg of the core.

10. The apparatus of claim 7 wherein a number of windings around the second leg of the core is not equal to a number of windings around the first leg of the core.

11. The apparatus of claim 6 wherein:
the first leg of the core is disposed at a fixed angle relative to the second leg of the core, and
the fixed angle at which the first leg of the core is disposed relative to the second leg of the core is other than 180°.

12. The apparatus of claim 6 wherein the mechanical coupling between the first leg of the core and the second leg of the core enables an angle at which the first leg of the core is disposed relative to the second leg of the core to be changed, thereby enabling the properties of the magnetic field to be changed by changing the angle at which the first leg of the core is disposed relative to the second leg of the core.

13. The apparatus of claim 6 wherein a length of the first leg of the core is substantially the same as a length of the second leg of the core.

14. The apparatus of claim 6 wherein a length of the first leg of the core is different than a length of the second leg of the core.

15. The apparatus of claim 1 further comprising a housing, wherein both the magnetic field generator and the fragrance delivery system are at least partially incorporated within the housing.

16. The apparatus of claim 15 wherein an opening is defined within the housing exposing at least a portion of the magnetic field generator to an exterior of the housing.

17. The apparatus of claim 16 wherein the magnetic field generator includes a conductive coil, at least a portion of which is incorporated within the housing.

18. The apparatus of claim 17 wherein:
the magnetic field generator further includes a core, at least a portion of which is incorporated within the housing, and
the conductive coil is wound around the core.

19. The apparatus of claim 15 wherein the housing is configured to receive a voltage source.

20. The apparatus of claim 19 further comprising a voltage source received within the housing, the voltage source having a positive terminal and a negative terminal, wherein the positive terminal of the voltage source is connected to a first terminal of the conductive coil and the negative terminal of the voltage source is connected to a second terminal of the conductive coil such that an electric current flows through the conductive coil between the first terminal and the second terminal thereby generating the magnetic field.

21. The apparatus of claim 1 further comprising a voltage source having a positive terminal and a negative terminal, wherein:
the fragrance delivery system includes a conductor for supplying an electrical bias to fragrant particles to be released by the fragrance delivery system, and
a first terminal of the conductor is electrically coupled to the negative terminal of the voltage source and a second terminal of the conductor provides an electrical bias to at least some of the fragrant particles to be released by the fragrance delivery system.

22. The apparatus of claim 1 further comprising an additional magnetic field generator that is configured to generate another magnetic field, that is physically distinct from the magnetic field generator, and that is located adjacent to the magnetic field generator, wherein:

the magnetic field generator and the other magnetic field generator are configured such that the magnetic field generated by the magnetic field generator and the other magnetic field generated by the other magnetic field generator are additive and combine to form a unique magnetic field, and at least some of the released fragrant particles enter the unique magnetic field.

23. The apparatus of claim 1 further comprising multiple additional magnetic field generators, each of which is configured to generate an additional magnetic field, is physically distinct from the magnetic field generator and other of the multiple additional magnetic field generators, and is displaced from other of the multiple additional magnetic field generators, wherein:

the magnetic field generator and the multiple additional magnetic field generators are configured to generate magnetic fields that are oriented such that at least some of the fragrant particles released into the magnetic field generated by the magnetic field generator are transferred to each of the additional magnetic fields.

24. The apparatus of claim 1 wherein the magnetic field generator and the fragrance delivery system are not physically connected.

25. An apparatus for fragrancing an air space comprising:
a magnetic field generator configured to generate a magnetic field; and
a fragrance delivery system configured to release fragrant particles into an air space such that at least some of the fragrant particles enter the magnetic field generated by the magnetic field generator, wherein:
the magnetic field generator includes a core and a conductive coil wound around the core,
the core includes a first leg and a second leg that is mechanically coupled to the first leg,
at least one winding of the conductive coil is wound around the first leg of the core, and
at least one winding of the conductive coil is wound around the second leg of the core.

26. The apparatus of claim 25 wherein:
the first leg of the core and the second leg of the core are formed from a contiguous piece of material,
the core includes a dividing post that bisects the contiguous piece of material thereby defining the first and second legs of the core,
the conductive coil is formed from a wire, the wire having a first end and a second end, and
from the perspective of the first end of the wire, the wire is wound around the first leg of the core before the wire is wound around the second leg of the core, with windings around the first leg of the core beginning adjacent to the dividing post and extending generally outwardly along the first leg of the core away from the dividing post and the second leg of the core before returning inwardly along the first leg of the core towards the dividing post and the second leg of the core and windings around the second leg of the core beginning adjacent to the dividing post and extending generally outwardly along the second leg of the core away from the dividing post and the first leg of the core before returning inwardly along the second leg of the core towards the dividing post and the first leg of the core.

27. The apparatus of claim 26 further comprising a voltage source having a positive terminal and a negative terminal, wherein:
the first end of the wire is electrically coupled to the negative terminal of the voltage source, and
the second end of the wire is electrically coupled to the positive terminal of the voltage source.

28. The apparatus of claim 26 wherein a number of windings around the first leg of the core is equal to a number of windings around the second leg of the core.

29. The apparatus of claim 26 wherein a number of windings around the second leg of the core is not equal to a number of windings around the first leg of the core.

30. The apparatus of claim 25 wherein:
the first leg of the core is disposed at a fixed angle relative to the second leg of the core, and
the fixed angle at which the first leg of the core is disposed relative to the second leg of the core is other than 180°.

31. The apparatus of claim 25 wherein the mechanical coupling between the first leg of the core and the second leg of the core enables an angle at which the first leg of the core is disposed relative to the second leg of the core to be changed, thereby enabling the properties of the magnetic field to be changed by changing the angle at which the first leg of the core is disposed relative to the second leg of the core.

32. The apparatus of claim 25 wherein a length of the first leg of the core is substantially the same as a length of the second leg of the core.

33. The apparatus of claim 25 wherein a length of the first leg of the core is different than a length of the second leg of the core.

34. An apparatus for fragrancing an air space comprising:
a magnetic field generator configured to generate a magnetic field;
a fragrance delivery system configured to release fragrant particles into an air space such that at least some of the fragrant particles enter the magnetic field generated by the magnetic field generator; and
a voltage source having a positive terminal and a negative terminal, wherein:
the fragrance delivery system includes a conductor for supplying an electrical bias to fragrant particles to be released by the fragrance delivery system, and
a first terminal of the conductor is electrically coupled to the negative terminal of the voltage source and a second terminal of the conductor provides an electrical bias to at least some of the fragrant particles to be released by the fragrance delivery system.

35. An apparatus for fragrancing an air space comprising:

a magnetic field generator configured to generate a magnetic field;

a fragrance delivery system configured to release fragrant particles into an air space such that at least some of the fragrant particles enter the magnetic field generated by the magnetic field generator; and an additional magnetic field generator that is configured to generate another magnetic field, that is physically distinct from the magnetic field generator, and that is located adjacent to the magnetic field generator, wherein:

the magnetic field generator and the other magnetic field generator are configured such that the magnetic field generated by the magnetic field generator and the other magnetic field generated by the other magnetic field generator are additive and combine to form a unique magnetic field, and at least some of the released fragrant particles enter the unique magnetic field.

36. An apparatus for fragrancing an air space comprising:

a magnetic field generator configured to generate a magnetic field;

a fragrance delivery system configured to release fragrant particles into an air space such that at least some of the fragrant particles enter the magnetic field generated by the magnetic field generator; and multiple additional magnetic field generators, each of which is configured to generate an additional magnetic field, is physically distinct from the magnetic field generator and other of the multiple additional magnetic field generators, and is displaced from other of the multiple additional magnetic field generators, wherein:

the magnetic field generator and the multiple additional magnetic field generators are configured to generate magnetic fields that are oriented such that at least some of the fragrant particles released into the magnetic field generated by the magnetic field generator are transferred to each of the additional magnetic fields.

* * * * *